(12) United States Patent
Wu et al.

(10) Patent No.: US 11,673,877 B2
(45) Date of Patent: *Jun. 13, 2023

(54) NIRAPARIB COMPOSITIONS

(71) Applicants: Tesaro, Inc., Waltham, MA (US); Merck Sharp & Dohme Corp., Rahway, NJ (US)

(72) Inventors: George Wu, Waltham, MA (US); John Chaber, Waltham, MA (US); Arlene E. McKeown, Rahway, NJ (US); Jennifer R. Foley, Rahway, NJ (US)

(73) Assignees: Tesaro, Inc., Wilmington, DE (US); Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/339,896

(22) Filed: Jun. 4, 2021

(65) Prior Publication Data

US 2021/0403448 A1 Dec. 30, 2021

Related U.S. Application Data

(63) Continuation of application No. 16/584,401, filed on Sep. 26, 2019, now Pat. No. 11,091,459, which is a continuation of application No. PCT/US2018/024603, filed on Mar. 27, 2018.

(60) Provisional application No. 62/477,411, filed on Mar. 27, 2017.

(51) Int. Cl.
| | |
|---|---|
| C07D 401/10 | (2006.01) |
| A61K 9/00 | (2006.01) |
| A61K 9/48 | (2006.01) |
| A61K 9/20 | (2006.01) |
| A61K 31/454 | (2006.01) |

(52) U.S. Cl.
CPC .......... *C07D 401/10* (2013.01); *A61K 9/0053* (2013.01); *A61K 9/20* (2013.01); *A61K 9/48* (2013.01); *C07B 2200/13* (2013.01)

(58) Field of Classification Search
CPC ...... C07D 401/10; A61K 9/0053; A61K 9/20; A61K 9/48; A61K 31/454; C07B 2200/13
See application file for complete search history.

(56) References Cited

U.S. PATENT DOCUMENTS

| | | | |
|---|---|---|---|
| 8,071,623 | B2 | 12/2011 | Jones et al. |
| 8,436,185 | B2 | 5/2013 | Foley et al. |
| 2010/0278921 | A1 | 11/2010 | Fischer et al. |
| 2010/0286157 | A1 | 11/2010 | Quiqley et al. |
| 2012/0214998 | A1 | 8/2012 | Bierlmaier et al. |
| 2015/0029916 | A1 | 1/2015 | Vukadinovic et al. |
| 2015/0110869 | A1 | 4/2015 | Philip et al. |
| 2015/0299219 | A1 | 10/2015 | Xi et al. |
| 2016/0045502 | A1 | 2/2016 | Brown |
| 2016/0051561 | A1 | 2/2016 | Etter |
| 2016/0339124 | A1 | 11/2016 | Mach et al. |
| 2017/0029428 | A1 | 2/2017 | Blatter et al. |
| 2018/0311224 | A1 | 11/2018 | Hedley et al. |
| 2019/0290629 | A1 | 9/2019 | Gan et al. |
| 2020/0017462 | A1 | 1/2020 | Wu et al. |
| 2020/0289494 | A1 | 9/2020 | McGurk et al. |
| 2021/0038585 | A1 | 2/2021 | McGurk et al. |

FOREIGN PATENT DOCUMENTS

| | | |
|---|---|---|
| CN | 101415686 | 4/2009 |
| CN | 106496187 | 3/2017 |
| CN | 106831708 | 6/2017 |
| CN | 106854176 | 6/2017 |
| CN | 108530425 | 9/2018 |
| EP | 2007733 | 12/2008 |
| JP | 2017516784 | 6/2017 |
| WO | WO 2007/113596 | 10/2007 |
| WO | WO 2008/043024 | 4/2008 |
| WO | WO 2008/084261 | 7/2008 |
| WO | WO 2009/087381 | 7/2009 |
| WO | WO 2014/088983 | 6/2014 |
| WO | WO 2014/088984 | 6/2014 |
| WO | WO 2016/028689 | 2/2016 |
| WO | WO 2016/094391 | 6/2016 |
| WO | WO 2018/005818 | 1/2018 |
| WO | WO 2018/108160 | 6/2018 |
| WO | WO 2018/122168 | 7/2018 |
| WO | WO 2018/183349 | 10/2018 |
| WO | WO 2018/183354 | 10/2018 |
| WO | WO 2018/200517 | 11/2018 |
| WO | WO 2018/208968 | 11/2018 |
| WO | WO 2018/213732 | 11/2018 |
| WO | WO 2019/067634 | 4/2019 |
| WO | WO 2019/067978 | 4/2019 |
| WO | WO 2019/071123 | 4/2019 |
| WO | WO 2019/133697 | 7/2019 |
| WO | WO 2019/152989 | 8/2019 |

OTHER PUBLICATIONS

Frolova et al., "PARP inhibitors in the treatment of metastatic breast cancer patients with germline BRCA1/2 mutations. Experience of treatment with talazoparib in clinical practice," Meditsinskiy Sovet, Jul. 2020, 9:57-61 (with English Abstract).
Huang et al., "PARP-1 suppresses adiponectin expression through poly (ADP-ribosyl)ation of PPARγ in cardiac fibroblasts," Cardiovascular Research, Sep. 2009, 81:98-107.
U.S. Appl. No. 62/489,415, filed Apr. 24, 2017, Stewart et al.
Chung et al., "Process Development of C—N Cross-Coupling and Enantioselective Biocatalytic Reactions for the Asymmetric Synthesis of Niraparib," Org. Process Res. Dev., 2014, 18:215-27.
Emmanuel et al. "Small Volume Dissolution Testing as a Powerful Method during Pharmaceutical Development", Pharmaceutics, 2010, 2:351-63.
Globalnewswire.com [online], "TESARO Announces Availability of Zejula™ (Niraparib) for Patients With Recurrent Ovarian Cancer in the U.S.", Apr. 19, 2017, retrieved on Jun. 6, 2020, retrieved from URL <https://www.globenewswire.com/news release/2017/04/19/962337/0/en/TESARO-Announces-Availability-of-Zejula-Niraparib-for-Patients-With-Recurrent-Ovarian-Cancer-in-the-U-S.html>, 7 pages.

(Continued)

*Primary Examiner* — John M Mauro
(74) *Attorney, Agent, or Firm* — Fish & Richardson P.C.

(57) ABSTRACT

The present invention relates to compositions comprising the compound niraparib, in particular certain solid forms of niraparib.

20 Claims, 9 Drawing Sheets

(56) References Cited

OTHER PUBLICATIONS

Hughes, "Patent review of manufacturing routes to recently approved PARP inhibitors: olaparib, rucaparib, and niraparib." Organic Process Research & Development 2017, 21(9):1227-1244.
Jones et al., "Discovery of 2-{4-[(3S)-piperidin-3-yl]phenyl}-2H-indazole-7-carboxamide (MK-4827): a novel oral poly(ADP-ribose)polymerase (PARP) inhibitor efficacious in BRCA-1 and -2 mutant tumors ," Journal Medicinal Chemistry, 2009, 52:7170-7185.
Kojima, "Targeting for Efficiency in Selecting Crystalline Form in Development of Medicine", Pharmacy, Sep. 2008, 68(5): 344-349, 22 pages (with machine translation).
Maruzen, "Pharmaceutical Crystallization Method and Diastereomer salt formation method for optical resolution Crystallization in place-Methods and applications-", Handbook of Preparation of Organic Compound Crystals—Principle and Know-How-, Jul. 2008, p. 57-84, 37 pages (with machine translation).
Ministry of Health, Labor, and Welfare, Commissioner of Pharmaceutical Safety Evaluation Division, "Residual Solvent Guidelines for Pharmaceutical Products", Pharmaceutical Evaluation, No. 307, 1998, pp. 1-11, 24 pages (with machine translation).
PCT International Preliminary Report on Patentability for International Application No. PCT/US2018/024597, dated Oct. 1, 2019, 11 pages.
PCT International Preliminary Report on Patentability in International Application No. PCT/US2018/024603, dated Jul. 20, 2018, 10 pages.
PCT International Search Report and Written Opinion in International Application No. PCT/US2018/024603, dated Jul. 20, 2018, 13 pages.
PCT International Search Report and Written Opinion in International Application No. PCT/US2018/024597, dated Jul. 27, 2018, 14 pages.
PCT International Search Report and Written Opinion in International Appln. No. PCT/US2018/052979, dated Jan. 2, 2019, 10 pages.
Takada, "Active Pharmaceutical Ingredient Form Screening and Selection in Drug Discovery Stage", Pharm Stage, Jan. 2007, 6(10):20-25, 22 pages (with machine translation).
Test 711 "Dissolution", the United States Pharmacopoeia 37th revision (USP 37, NF 32): United States Pharmacopoeia, Convention, Inc., Rockville, Md., 2014 ("USP 711"), pp. 344-351.
Wallace et al., "Development of a Fit-for-Purpose Large-Scale Synthesis of an Oral PARP Inhibitor," Org, Process Res. Dev., 2011, 15:831-840.
Zejula Patient Information approved by the U.S. Food and Drug Administration, Mar. 2017.
U.S. Appl. No. 16/584,149, filed Sep. 26, 2019, Simon McGurk.
U.S. Appl. No. 17/073,198, filed Oct. 16, 2020, Simon McGurk.
U.S. Appl. No. 16/650,948, filed Mar. 26, 2020, Simon McGurk.
U.S. Appl. No. 16/967,351, filed Aug. 4, 2020, Simon McGurk.
Wikipedia.org [online], "Carr index," Aug. 17, 2021, retrieved on Mar. 28, 2022, retrieved from URL <https://en.wikipedia.org/w/index.php?title=Carr_index&oldid=1039190201>, 2 pages.
Davis et al., "Ewing sarcoma in adolescents and young adults: diagnosis and treatment," Clinical Oncology in Adolescents and Young Adults, 2014, 4:21-31.
Handbook of Pharmaceutical Excipients, 6th ed., 2009, pp. 364-369, 404-407.
Immunotherapy of Cancer, 2017, 28(Supplement 5), 420, 1185P.
Immunotherapy of Cancer, 2017, 28(Supplement 5), 406-407, 1143PD.
Mariappan et al., "Emerging treatment options for ovarian cancer focus on rucaparib," International Journal of Women's Health, 2017, 9:913-924.
Ohmoto et al., "Current status of poly(ADP-ribose) polymerase inhibitors and future directions," Onco Targets and Therapy, 2017, (10):5195-5208.
Ring et al., "Checkpoint Proteins in Pediatric Brain and Extracranial Solid Tumors: Opportunities for Immunotherapy," Clin Cancer Res., Jan. 15, 2017, 23(2): 342-350.
Shekunov et al., "Particle Size Analysis in Pharmaceutics: Principles, Methods and Applications," Pharmaceutical Research, Feb. 2007, 24(2):203-227.
www.colorcon.com [online], "Elegant Film Coating Systems Delivering High Adhesion Quality Finish and Manufacturing Efficiency," High Performance Film Coating Systems Brochure, Nov. 9, 2022, retrieved Nov. 16, 2022, retrieved from URL<https://www.colorcon.com/jp/markets/pharmaceuticals/film-coatings/immediate-release/opadry-ii/download/31/2641/34?method=view>, 2 pages.

NIRAPARIB COMPOSITIONS

CROSS REFERENCE

This application is a continuation of U.S. patent application Ser. No. 16/584,401, filed Sep. 26, 2019; which is a continuation of International Application No. PCT/US2018/024603, filed Mar. 27, 2018, which claims the benefit of U.S. Provisional Application No. 62/477,411, filed Mar. 27, 2017, each of which is incorporated herein by reference in its entirety.

Niraparib is an orally active and potent poly (ADP-ribose) polymerase, or PARP, inhibitor. Niraparib and pharmaceutically acceptable salts thereof, are disclosed in International Publication No. WO2007/113596 and European Patent No. EP2007733B1; International Publication No. WO2008/084261 and U.S. Pat. No. 8,071,623; and International Publication No. WO2009/087381 and U.S. Pat. No. 8,436,185. Methods of making niraparib and pharmaceutically acceptable salts thereof are disclosed in international Publication Nos. WO2014/088983 and WO2014/088984. Methods to treat cancer with niraparib and pharmaceutically acceptable salts thereof are disclosed in U.S. Provisional Patent Application Nos. 62/356,461, 62/402,427, 62/470,141, and PCT application PCT/US17/40039. The contents of each of the foregoing references are incorporated herein by reference in their entirety.

PARP is a family of proteins involved in many functions in a cell, including DNA repair, gene expression, cell cycle control, intracellular trafficking and energy metabolism. PARP proteins play key roles in single strand break repair through the base excision repair pathway. PARP inhibitors have shown activity as a monotherapy against tumors with existing DNA repair defects, such as BRCA1 and BRCA2, and as a combination therapy when administered together with anti-cancer agents that induce DNA damage.

Despite several advances in treatment of ovarian cancer, most patients eventually relapse, and subsequent responses to additional treatment are often limited in duration. Women with germline BRCA1 or BRCA2 mutations have an increased risk for developing high grade serous ovarian cancer (HGSOC), and their tumors appear to be particularly sensitive to treatment with a PARP inhibitor. In addition, published scientific literature indicates that patients with platinum sensitive HGSOC who do not have germline BRCA1 or BRCA2 mutations may also experience clinical benefit from treatment with a PARP inhibitor.

It is estimated that 5% to 10% of women who are diagnosed with breast cancer, or more than 15,000 women each year, carry a germline mutation in either their BRCA1 or BRCA2 genes. The development of cancer in these women involves the dysfunction of a key DNA repair pathway known as homologous recombination. While cancer cells can maintain viability despite disruption of the homologous recombination pathway, they become particularly vulnerable to chemotherapy if an alternative DNA repair pathway is disrupted. This is known as synthetic lethality a situation where the individual loss of either repair pathway is compatible with cell viability; but the simultaneous loss of both pathways results in cancer cell deaths. Since PARP inhibitors block DNA repair, in the context of cancer cells with the BRCA mutation, PARP inhibition results in synthetic lethality. For this reason, patients with germline mutations in a BRCA gene show marked clinical benefit that follows treatment with a PARP inhibitor.

One embodiment provides a composition comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide. Another embodiment provides the composition wherein the crystalline Form I of 2-{4-[(3S)-piperidin-3-yl]phenyl}-2H-indazole-7-carboxamide has an X-ray powder diffraction pattern substantially as shown in FIG. 1. Another embodiment provides the composition where the crystalline Form I of 2-{4-[(3S)-piperidin-3-yl]phenyl}-2H-indazole-7-carboxamide is characterized by at least one X-ray diffraction pattern reflection selected from a 2θ value of 9.5±0.2, 12.4±0.2, 13.2±0.2, 17.4±0.2, 18.4±0.2, 21.0±0.2, 24.9±0.2, 25.6±0.2, 26.0±0.2, and 26.9±0.2. Another embodiment provides the composition wherein the crystalline Form I of 2-{4-[(3S)-piperidin-3-yl]phenyl}-2H-indazole-7-carboxamide is characterized by an X-ray diffraction pattern reflection at 2θ=24.9±0.2. Another embodiment provides the composition wherein the crystalline Form I is characterized by X-ray diffraction pattern reflections at 2θ values of 9.5±0.2 and 26.0±0.2. Another embodiment provides the composition wherein the crystalline Form I is characterized by X-ray diffraction pattern reflections at 2θ values of 12.4±0.2, 13.2±0.2, 17.4±0.2, 18.4±0.2, 21.0±0.2, 25.6±0.2, and 26.9±0.2. Another embodiment provides the composition wherein the crystalline Form I is characterized by at least one X-ray diffraction pattern reflection selected from a 2θ value of 12 4±0.2, 13.2±0.2, 17.4±0.2, 18.4±0.2, 21.0±10.2, 25.6±0.2, and 26.9±0.2. Another embodiment provides the composition wherein the crystalline Form I is characterized by at least two X-ray diffraction pattern reflections selected from a 2θ value of 12 4±0.2, 13 2±0.2, 17.4±0.2, 18.4±0.2, 21.0±0 2, 25.6±0 2, and 26.9±0.2 Another embodiment provides the composition wherein the crystalline Form 1 is characterized by at least three X-ray diffraction pattern reflections selected from a 2θ value of 12.4±0.2, 13 2±0.2, 17.4±0.2, 18.4±0.2, 21.0±0.2, 25.6±0.2, and 26.9±0.2. Another embodiment provides the composition wherein the crystalline Form I is characterized by at least four X-ray diffraction pattern reflections selected from a 2θ value of 12.4±0.2, 13.2±0.2, 17.4±0.2, 18.4±0.2, 21.0±0.2, 25.6±0.2, and 26.9±0.2. Another embodiment provides the composition wherein the crystalline Form I is characterized by a scanning differential calorimetry pattern substantially as shown in FIG. 2. Another embodiment provides the composition wherein the crystalline Form I is characterized by a Raman spectroscopy pattern substantially as shown in FIG. 3. Another embodiment provides the composition wherein the crystalline Form I is characterized by an infrared spectroscopy pattern substantially as shown in FIG. 4. Another embodiment provides the composition wherein the crystalline Form I is characterized by a dynamic water vapor sorption pattern substantially as shown in FIG. 5. Another embodiment provides the composition wherein the presence of Form III is characterized by at least one X-ray diffraction pattern reflection selected from a 2θ value of 17.8±0.2, 19.0±0.2, or 22.8±0.2.

Another embodiment provides the composition wherein substantially free of Form II and Form III means less than about 20% (w/w) combined total weight for Form II and Form I compared to the combined total weight of Form I, Form II and Form III. Another embodiment provides the composition wherein substantially free of Form II and Form III means less than about 15% (w/w) combined total weight for Form II and Form III compared to the combined total weight of Form I, Form II and Form III. Another embodiment provides the composition wherein substantially free of Form II and Form III means less than about 10% (w/w) combined total weight for Form II and Form III compared to the combined total weight of Form I, Form II and Form III. Another embodiment provides the composition wherein substantially free of Form II and Form III means less than about 8% (w/w) combined total weight for Form II and Form II compared to the combined total weight of Form I, Form II and Form III. Another embodiment provides the composition wherein substantially free of Form II and Form II means less than about 6% (w/w) combined total weight for Form II and Form III compared to the combined total weight of Form I, Form II and Form III. Another embodiment provides the composition wherein substantially free of Form II and Form III means less than about 4% (w/w) combined total weight for Form II and Form III compared to the combined total weight of Form I, Form II and Form III. Another embodiment provides the composition wherein substantially free of Form II and Form III means less than about 3% (w/w) combined total weight for Form II and Form III compared to the combined total weight of Form I, Form II and Form III. Another embodiment provides the composition wherein substantially free of Form II and Form III means less than about 2% (w/w) combined total weight for Form II and Form III compared to the combined total weight of Form I, Form II and Form III. Another embodiment provides the composition wherein substantially free of Form II and Form III means less than about 1% (w/w) combined total weight for Form II and Form III compared to the combined total weight of Form I, Form II and Form III.

One embodiment provides a composition comprising crystalline Form II of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide and crystalline Form III of 2-{4-[(3S)-piperidin-3-yl]phenyl}-2H-indazole-7-carboxamide. One embodiment provides a composition comprising crystalline Form II of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide. One embodiment provides a composition comprising crystalline Form II 2-{4-[(3S)-piperidin-3-yl]phenyl}-2H-indazole-7-carboxamide and crystalline Form III of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide. In one embodiment, crystalline Form II is characterized by at least one X-ray diffraction pattern reflection selected from a 2θ value of 9.7±0.3, 12.8±0.3, 17.9±0.3, 19.7±0.3, and 21.8±0.3. In one embodiment, crystalline Form II has an X-ray powder diffraction pattern substantially as shown in FIG. 9 for Form II.

One embodiment provides a composition comprising crystalline Form III of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide and crystalline Form II of 2-{4-[(3S)-piperidin-3-yl]phenyl}-2H-indazole-7-carboxamide. One embodiment provides a composition comprising crystalline Form III of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide. One embodiment provides crystalline Form III characterized by at least one X-ray diffraction pattern reflection selected from a 2θ value of 17.8±0.2, 19.0±0.2, or 22.8±0.2. One embodiment provides crystalline Form II that has an X-ray powder diffraction pattern substantially as shown in FIG. 9 for Form III. One embodiment provides crystalline Form III of 2-{4-[(3S)-piperidin-3-yl]phenyl}-2H-indazole-7-carboxamide that has an X-ray powder diffraction pattern substantially as shown in FIG. 7. One embodiment provides crystalline Form III of 2-{4-[(3S)-piperidin-3-yl]phenyl}-2H-indazole-7-carboxamide characterized by a dynamic water vapor sorption pattern substantially as shown in FIG. 8. One embodiment provides crystalline Form I of 2-{4-[(3S)-piperidin-3-yl]phenyl}-2H-indazole-7-carboxamide characterized by a scanning differential calorimetry pattern substantially as shown in FIG. 2.

One embodiment provides a method of making crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide, comprising dissolving a composition comprising Form II of 2-{4-[(3S)-piperidin-3-yl]phenyl}-2H-indazole-7-carboxamide or Form III of 2-{4-[(3S)-piperidin-3-yl]phenyl}-2H-indazole-7-carboxamide, or a mixture thereof, in a solvent having a water:organic solvent ratio of about 10:1 to about 400:1 (v/v), and crystallizing the crystalline Form I. Another embodiment provides the method wherein the water:organic solvent ratio is about 10:1 (v/v), about 50:1 (v/v), about 100:1 (v/v), about 200:1 (v/v), about 300:1 (v/v), or about 400:1 (v/v). Another embodiment provides the composition wherein the organic solvent is a polar solvent, a polar protic solvent, a polar aprotic solvent, an ether-containing solvent, or any combination thereof. Another embodiment provides the composition wherein the organic solvent is 2-propanol, acetone, methyl ethyl ketone, acetonitrile, acetic acid, formic acid, methyl tert-butyl ether, dioxane, dimethyl sulfoxide, or any combination thereof. Another embodiment provides the composition wherein the organic solvent is acetone, methyl ethyl ketone, acetonitrile, methyl tert-butyl ether, dioxane, dimethyl sulfoxide, or any combination thereof. Another embodiment provides the composition wherein the organic solvent is 2-propanol, acetic acid, formic acid, or any combination thereof. Another embodiment provides the composition wherein the organic solvent and water is heated prior to crystallization.

One embodiment provides a composition comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide prepared by dissolving a composition comprising Form II of 2-{4-[(3S)-piperidin-3-yl]phenyl}-2H-indazole-7-carboxamide or Form III of 2-{4-[(3S)-piperidin-3-yl]phenyl}-2H-indazole-7-carboxamide, or a mixture thereof, in a solvent having a water:organic solvent ratio of about 10:1 to about 400:1 (v/v), and crystallizing the crystalline Form I. Another embodiment provides the composition wherein the water:organic solvent ratio is about 10:1 (v/v), about 50:1 (v/v), about 100:1 (v/v), about 200:1 (v/v), about 300:1 (v/v), or about 400:1 (v/v). Another embodiment provides the composition wherein the organic solvent is a polar solvent, a polar protic solvent, a polar aprotic solvent, an ether-containing solvent, or any combination thereof. Another embodiment provides the composition wherein the organic solvent is 2-propanol, acetone, methyl ethyl ketone, acetonitrile, acetic acid, formic acid, methyl tert-butyl ether, dioxane, dimethyl sulfoxide, or any combination thereof. Another embodiment provides the composition wherein the organic solvent is acetone, methyl ethyl ketone, acetonitrile, methyl tert-butyl ether, dioxane, dimethyl sulfoxide, or any combination thereof. Another embodiment provides the composition wherein the organic solvent is 2-propanol, acetic acid, formic acid, or any combination thereof. Another embodiment provides the composition wherein the organic solvent and water is heated prior to crystallization.

In some embodiments, a composition described herein is a pharmaceutical composition (e.g., a pharmaceutical composition comprising at least one pharmaceutically acceptable excipient). One embodiment provides a pharmaceutical composition comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide, and at least one pharmaceutically acceptable excipient. Another embodiment provides the pharmaceutical composition wherein the composition is in an oral dosage form. Another embodiment provides the pharmaceutical composition wherein the oral dosage form is a tablet or capsule. One embodiment provides an article of manufacture comprising multiple unit doses of the pharmaceutical composition in a sealed container with written instructions for use. In another embodiment, the article of manufacture comprising multiple unit doses of the pharmaceutical composition in a sealed container with written instructions for use, further comprises an induction seal, desiccant, or any combination thereof.

One embodiment provides a method for treating cancer in a patient in need thereof comprising administering to said patient a therapeutically effective amount of the pharmaceutical composition comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide, and at least one pharmaceutically acceptable excipient, wherein the cancer is selected from the group consisting of ovarian cancer, breast cancer, cervical cancer, endometrial cancer, prostate cancer, testicular cancer, pancreatic cancer, esophageal cancer, head and neck cancer, gastric cancer, bladder cancer, lung cancer, bone cancer, colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma, bladder cancer, liver cancer, kidney cancer, myeloma, lymphoma, and combinations thereof.

One embodiment provides a method for treating cancer in a patient having been diagnosed with cancer comprising administering to said patient a therapeutically effective amount of the pharmaceutical comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide, and at least one pharmaceutically acceptable excipient, wherein the cancer is selected from the group consisting of ovarian cancer, breast cancer, cervical cancer, endometrial cancer, prostate cancer, testicular cancer, pancreatic cancer, esophageal cancer, head and neck cancer, gastric cancer, bladder cancer, lung cancer, bone cancer, colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma, bladder cancer, liver cancer, kidney cancer, myeloma, lymphoma, and combinations thereof. Another embodiment provides the method wherein the cancer is selected from the group consisting of ovarian cancer, fallopian tube cancer, primary peritoneal cancer, and combinations thereof. Another embodiment provides the method wherein the cancer is a recurrent cancer. Another embodiment provides the method wherein the subject is a human subject. Another embodiment provides the method wherein the human subject was previously treated with a chemotherapy. Another embodiment provides the method wherein the chemotherapy is a platinum-based chemotherapy. Another embodiment provides the method wherein the human subject had a complete or partial response to the chemotherapy. Another embodiment provides the method wherein the pharmaceutical composition is administered once per day, twice per day, three times per day, or four times per day. Another embodiment provides the method wherein the pharmaceutical composition is administered once per week, twice per week, three times per week, or four times per week. Another embodiment provides the method wherein the pharmaceutical composition is administered every other day. Another embodiment provides the method wherein the pharmaceutical composition is administered once per day. Another embodiment provides the method wherein the total dose of a the pharmaceutical composition administered within a 24 hour period is about 1 mg to about 1000 mg. Another embodiment provides the method wherein the total dose is about 1000 mg, about 900 mg, about 800 mg, about 700 mg, about 600 mg, about 500 mg, about 400 mg, about 300 mg, about 200 mg, about 100 mg, about 90 mg, about 80 mg, about 70 mg, about 60 mg, about 50 mg, about 40 mg, about 30 mg, about 20 mg, about 10 mg, about 5 mg, or about 1 mg. Another embodiment provides the method wherein the pharmaceutical composition is administered once per day and the total daily dose is about 300 mg. Another embodiment provides the method wherein the administration is oral administration.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
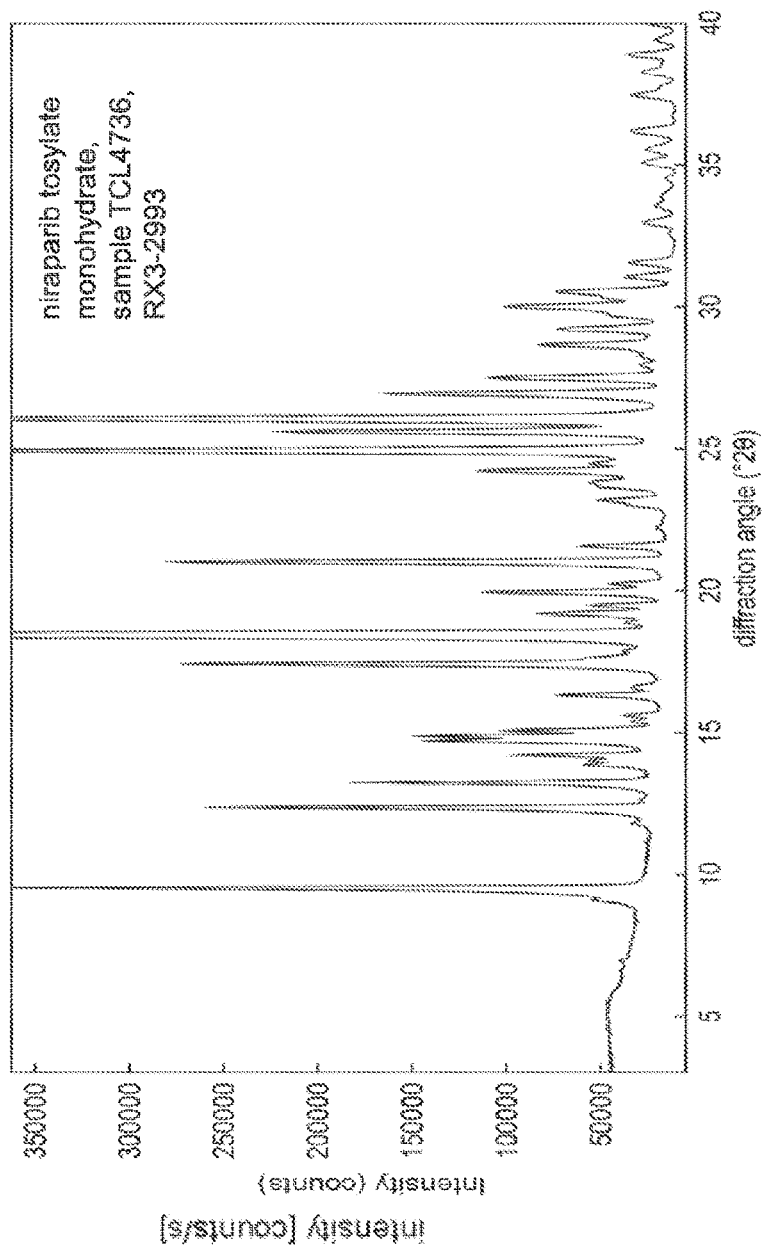
FIG. 1 shows an exemplary X-ray powder diffraction pattern for crystalline Form I of 2-{4-[(3S)-piperidin-3-yl]phenyl}-2H-indazole-7-carboxamide.

The term "cancer" includes both solid tumors and hematological malignancies. Cancers include, but are not limited to, ovarian cancer, breast cancer, cervical cancer, endometrial cancer, prostate cancer, testicular cancer, pancreatic cancer, esophageal cancer, head and neck cancer, gastric cancer, bladder cancer, lung cancer (e.g., adenocarcinoma, NSCLC and SCLC), bone cancer (e.g., osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g., liposarcoma), bladder cancer, liver cancer (e.g., hepatocellular carcinoma), kidney cancer (e.g., renal cell carcinoma), myeloid disorders (e.g., AML, CML, myelodysplastic syndrome and promyelocytic leukemia), and lymphoid disorders (e.g., leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma).

The term "composition", as in pharmaceutical composition, is intended to encompass a dug product comprising niraparib or its pharmaceutically acceptable salts, esters, solvates, polymorphs, stereoisomers or mixtures thereof, and the other inert ingredient(s) (pharmaceutically acceptable excipients). Such pharmaceutical compositions are synonymous with "formulation" and "dosage form". Pharmaceutical compositions of the invention include, but are not limited to, granules, tablets (single layered tablets, multi-layered tablets, mini tablets, bioadhesive tablets, caplets, matrix tablets, tablet within a tablet, mucoadhesive tablets, modified release tablets, orally disintegrating tablets, pulsatile release tablets, timed release tablets, delayed release, controlled release, extended release and sustained release tablets), capsules (hard and soft or liquid filled soft gelatin capsules), pills, troches, sachets, powders, microcapsules, minitablets, tablets in capsules and microspheres, matrix composition and the like. In some embodiments, the pharmaceutical composition refers to capsules. In some embodiments, the pharmaceutical composition refers to hard gelatin capsules or HPMC based capsules. In some embodiments, the pharmaceutical composition refers to hard gelatin capsules.

"Diluents" increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pact (Amstar); mannitol, hydroxypropylmethylcellulose, hydroxypropylmethylcellulose acetate stearate, sucrose-based diluents, confectioner's sugar, monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like. Combinations of one or more diluents can also be used.

The terms "effective amount" or "therapeutically effective amount," as used herein, refer to a sufficient amount of the niraparib being administered that would be expected to relieve to some extent one or more of the symptoms of the disease or condition being treated. For example, the result of administration of niraparib disclosed herein is reduction and/or alleviation of the signs, symptoms, or causes of cancer. For example, an "effective amount" for therapeutic uses is the amount of niraparib, including a formulation as disclosed herein required to provide a decrease or amelioration in disease symptoms without undue adverse side effects. The term "therapeutically effective amount" includes, for example, a prophylactically effective amount. It is understood that an "an effective amount" or a "therapeutically effective amount" varies, in some embodiments, from subject to subject, due to variation in metabolism of the compound administered, age, weight, general condition of the subject, the condition being treated, the severity of the condition being treated, and the judgment of the prescribing physician.

The terms "enhance" or "enhancing" refers to an increase or prolongation of either the potency or duration of a desired effect of niraparib, or a diminution of any adverse symptomatology that is consequent upon the administration of the therapeutic agent. Thus, in regard to enhancing the effect of niraparib disclosed herein, the term "enhancing" refers to the ability to increase or prolong, either in potency or duration, the effect of other therapeutic agents that are used in combination with niraparib disclosed herein. An "enhancing-effective amount," as used herein, refers to an amount of niraparib or other therapeutic agent which is adequate to enhance the effect of another therapeutic agent or niraparib in a desired system. When used in a patient, amounts effective for this use will depend on the severity and course of the disease, disorder or condition, previous therapy, the patient's health status and response to the drugs, and the judgment of the treating physician.

The term "excipient" means a pharmacologically inactive component such as a diluent, lubricant, surfactant, carrier, or the like. Excipients that are useful in preparing a pharmaceutical composition are generally safe, non-toxic and are acceptable for human pharmaceutical use. Reference to an excipient includes both one and more than one such excipient. Co-processed excipients are also covered under the scope of present invention.

"Filling agents" or "fillers" include compounds such as lactose, lactose monohydrate, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, magnesium stearate, calcium hydroxide, talc, sodium stearyl fumarate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

The term "subject" is used to mean an animal, preferably a mammal, including a human or non-human. The terms patient and subject may be used interchangeably.

A "therapeutically effective amount" or "effective amount" is that amount of a pharmaceutical agent to achieve a pharmacological effect. The term "therapeutically effective amount" includes, for example, a prophylactically effective amount. An "effective amount" of niraparib is an amount needed to achieve a desired pharmacologic effect or therapeutic improvement without undue adverse side effects. The effective amount of a niraparib will be selected by those skilled in the art depending on the particular patient and the disease. It is understood that "an effective amount" or a "therapeutically effective amount" can vary from subject to subject, due to variation in metabolism of niraparib, age, weight, general condition of the subject, the condition being treated, the severity of the condition being treated, and the judgment of the prescribing physician. As used herein, amelioration or lessening of the symptoms of a particular disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

The terms "treat," "treating" or "treatment," as used herein, include alleviating, abating or ameliorating a disease or condition, for example cancer, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

As used herein, "weight percent," "wt %," "percent by weight," "% by weight," and variations thereof refer to the concentration of a substance as the weight of that substance divided by the total weight of the composition and multiplied by 100.

Other objects, features, and advantages of the methods and compositions described herein will become apparent from the following detailed description. It should be understood, however, that the detailed description and the specific examples, while indicating specific embodiments, are given by way of illustration only.

Niraparib and Solid State Forms Thereof

The present invention relates to solid dosage forms of niraparib and pharmaceutically acceptable salts thereof (e.g., niraparib tosylate monohydrate), including solid forms having desirable characteristics favorable for pharmaceutical development. Niraparib has the following structure:

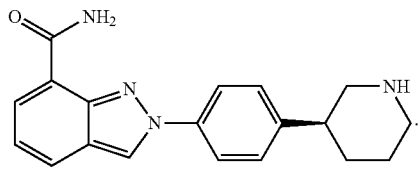 [SMILES: NC(=O)c1cccc2cn(-c3ccc([C@@H]4CCCNC4)cc3)nc12]

Niraparib is an orally available, selective poly(ADP-ribose) polymerase (PARP) 1 and 2 inhibitor. Niraparib displays PARP 1 and 2 inhibition with $IC_{50}$=3.8 and 2.1 nM, respectively, and in a whole cell assay, it inhibited PARP activity with $EC_{50}$=4 nM and inhibited proliferation of cancer cells with mutant BRCA-1 and BRCA-2 with $CC_{50}$ in the 10-100 nM range (see Jones et al., Journal Medicinal Chemistry, 2009, 52, 7170-7185). Methods of administering niraparib to cancer patients are also described in WO2018/005818, which is hereby incorporated by reference in its entirety.

The chemical name for niraparib tosylate monohydrate is 2-{4-[(3S)-piperidin-3-yl]phenyl}-2H-indazole 7-carboxamide 4-methylbenzenesulfonate hydrate (1:1.1) and it has the following chemical structure:

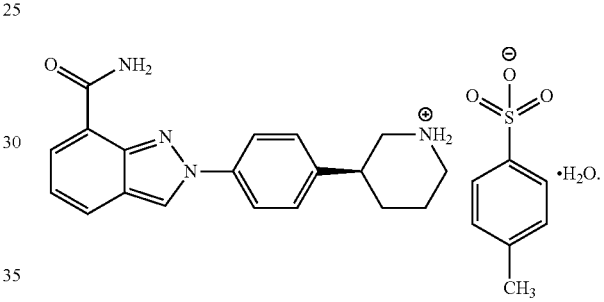

The empirical molecular formula for niraparib is $C_{26}H_{30}N_4O_5S$ and its molecular weight is 510.61 g/mol. Niraparib tosylate monohydrate drug substance is a white to off-white, non-hygroscopic crystalline solid. Niraparib solubility is pH independent below the pKa of 9.95, with an aqueous free base solubility of 0.7 mg/mL to 1.1 mg/mL across the physiological pH range.

Methods for preparation of niraparib include those described in WO 2014/088983; WO 2014/088984; U.S. Pat. Nos. 8,071,623; 8,436,185, U.S. 62/489,415 filed Apr. 24, 2017; and Jones et al., *J. Med Chem.*, 52:7170-7185, 2009, each of which is incorporated by reference in its entirety. Niraparib prepared according to these methods can be used in the methods of preparation of the crystalline solid forms described herein. For example, crystalline Form I of 2-{4-[(3S)-piperidin-3-yl]phenyl}-2H-indazole-7-carboxamide can be prepared from solvent systems comprising water (e.g., as described in Example 1 and Example 2). Crystalline Form II of 2-{4-[(3S)-piperidin-3-yl]phenyl}-2H-indazole-7-carboxamide can be produced under anhydrous conditions. Crystalline Form III of 2-{4-[(3S)-piperidin-3-yl]phenyl}-2H-indazole-7-carboxamide can be produced from crystalline Form I under heating conditions (e.g., as described in Example 3).

Provided herein are crystalline solid forms of 4-toluenesufonate salts of 2-{4-[(3S)-piperidin-3-yl]-2H-indazole-7-carboxamide. For example, provided herein are crystalline solid forms of 4-toluenesufonate salts of 2-{4-[(3S)-piperidin-3-yl]phenyl}-2H-indazole-7-carboxamide having 1:1 stoichiometry.

Figure 2:
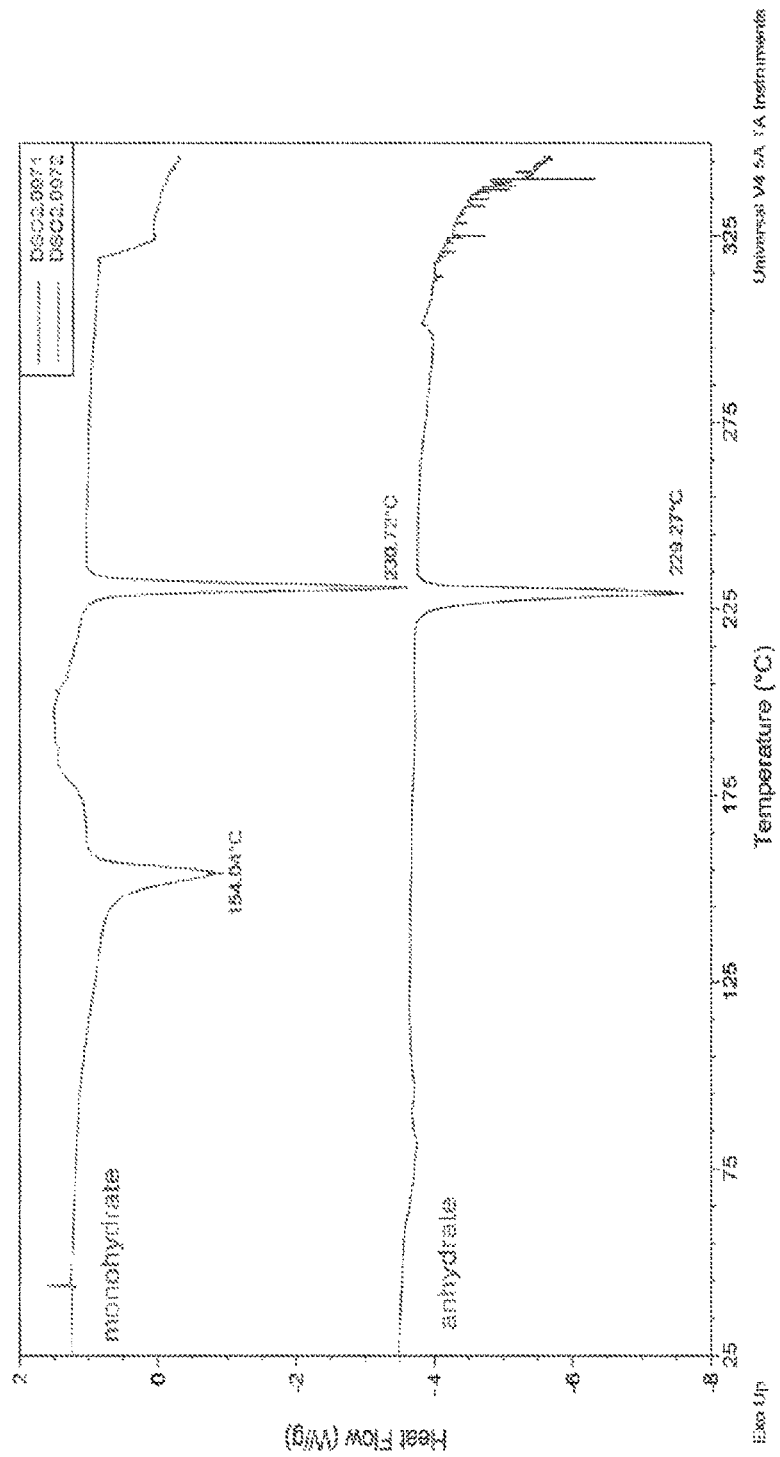
FIG. 2 shows an exemplary scanning differential calorimetry pattern for crystalline monohydrate Form I of 2-{4-[(3S)-piperidin-3-yl]phenyl}-2H-indazole-7-carboxamide and crystalline anhydrous Form III of 2-{4-[(3S)-piperidin-3-yl]phenyl}-2H-indazole-7-carboxamide.
Figure 3:
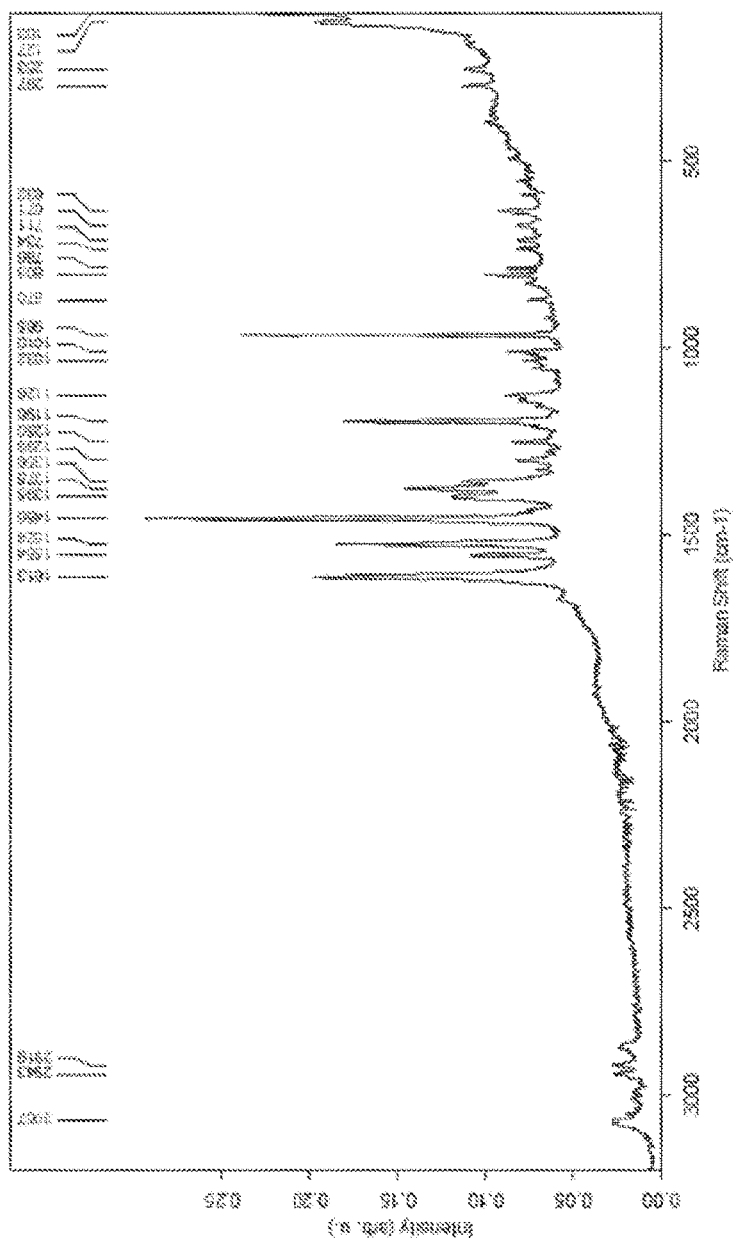
FIG. 3 shows an exemplary Raman spectroscopy pattern for crystalline Form I of 2-{4-[(3S)-piperidin-3-yl]phenyl}-2H-indazole-7-carboxamide.
Figure 4:
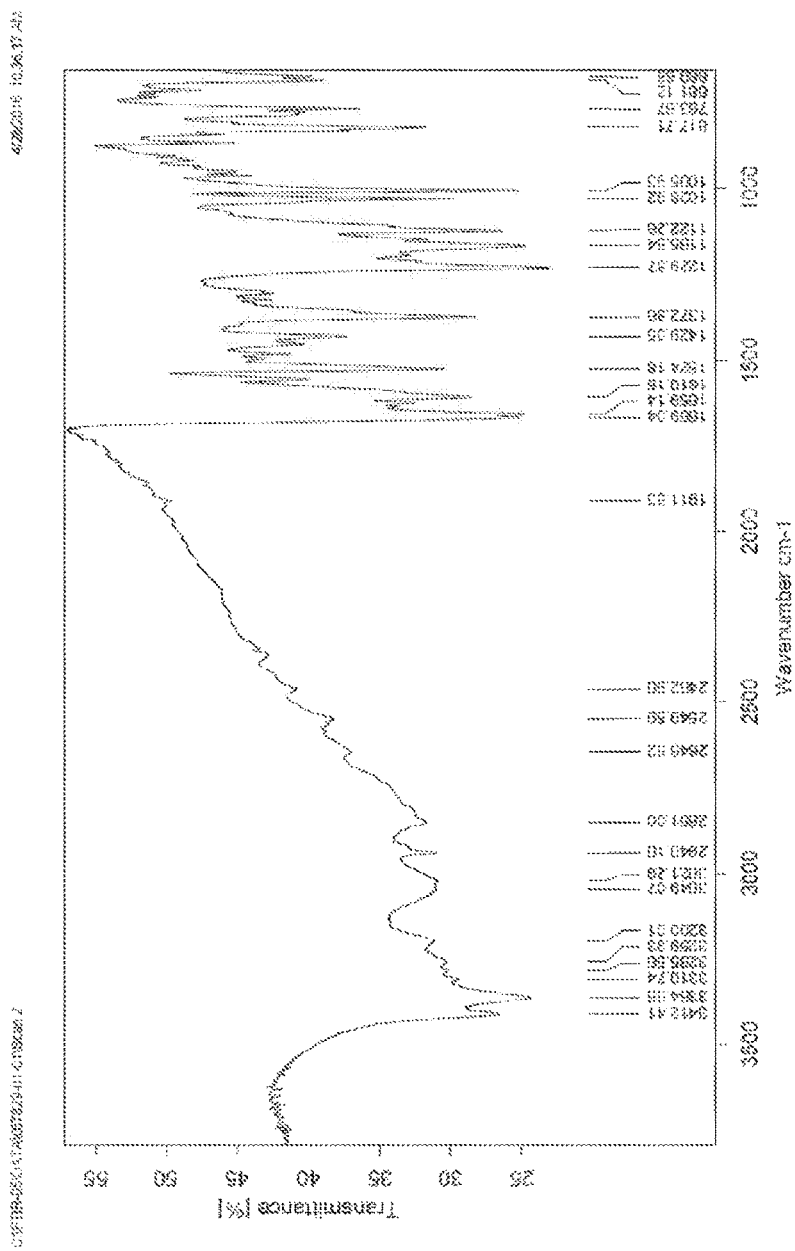
FIG. 4 shows an exemplary infrared spectroscopy pattern for crystalline Form I of 2-{4-[(3S)-piperidin-3-yl]phenyl}-2H-indazole-7-carboxamide.
Figure 5:
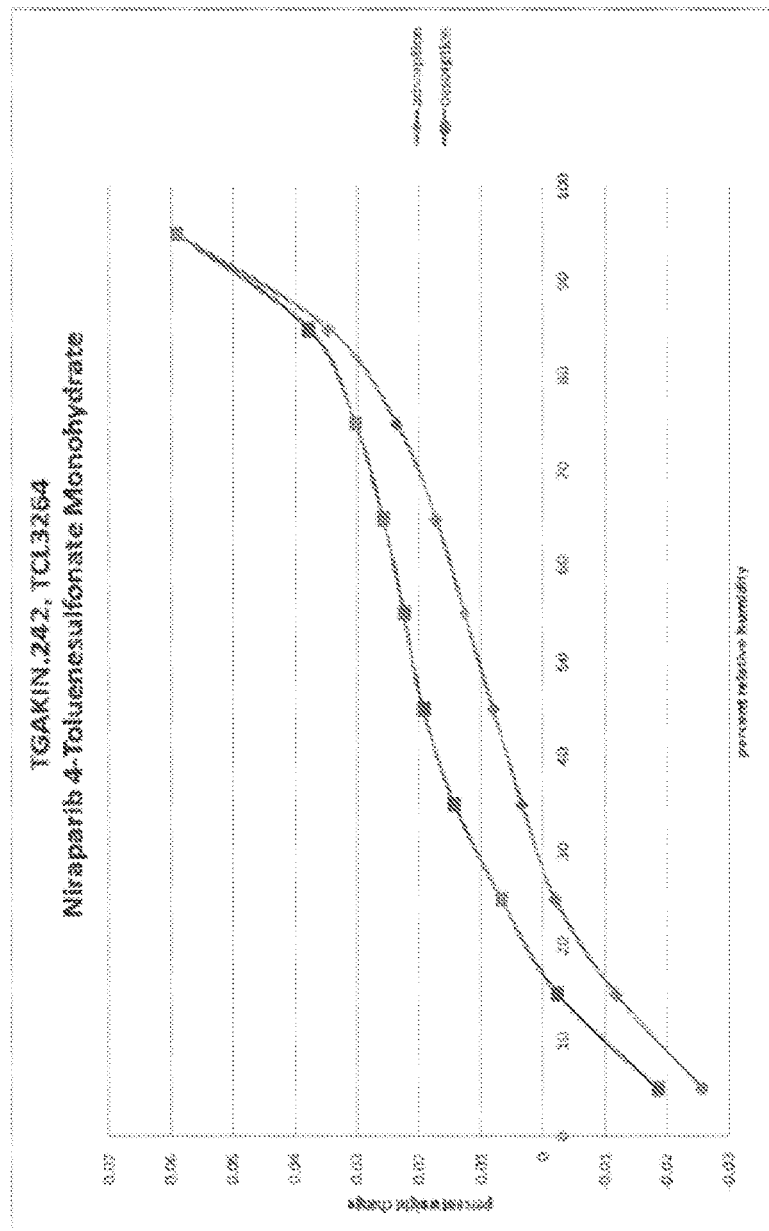
FIG. 5 shows an exemplary dynamic water vapor sorption pattern for crystalline Form I of 2-{4-[(3S)-piperidin-3-yl]phenyl}-2H-indazole-7-carboxamide.

Provided herein is crystalline Form I of 2-{4-[(3S)-piperidin-3-yl]phenyl}-2H-indazole-7-carboxamide. Crystalline Form I of 2-{4-[(3S)-piperidin-3-yl]phenyl}-2H-indazole-7-carboxamide is the 4-toluenesulfonate salt and is a monohydrate. Crystalline Form I of 2-{4-[(3S)-piperidin-3-yl]phenyl}-2H-indazole-7-carboxamide is also referred to by interchangeable terms such as: Form I of 2-{4-[(3S)-piperidin-3-yl]phenyl}-2H-indazole-7-carboxamide; crystalline monohydrate Form I of 2-{4-[(3S)-piperidin-3-yl]phenyl}-2H-indazole-7-carboxamide; crystalline Form I of niraparib tosylate monohydrate; crystalline Form I; or Form I. Exemplary X-ray powder diffraction data for Form I is provided in FIG. 1 and FIG. 6. FIG. 2 shows an exemplary scanning differential calorimetry pattern for crystalline Form I of 2-{4-[(3S)-piperidin-3-yl]phenyl}-2H-indazole-7-carboxamide. FIG. 3 shows an exemplary Raman spectroscopy pattern for crystalline Form I of 2-{4-[(3S)-piperidin-3-yl]phenyl}-2H-indazole-7-carboxamide. FIG. 4 shows an exemplary infrared spectroscopy pattern for crystalline Form I of 2-{4-[(3S)-piperidin-3-yl]phenyl}-2H-indazole-7-carboxamide. FIG. 5 shows an exemplary dynamic water vapor sorption pattern for crystalline Form I of 2-{4-[(3S)-piperidin-3-yl]phenyl}-2H-indazole-7-carboxamide.

Provided herein is crystalline Form II of 2-{4-[(3S)-piperidin-3-yl]phenyl}-2H-indazole-7-carboxamide. Crystalline Form II of 2-{4-[(3S)-piperidin-3-yl]phenyl}-2H-indazole-7-carboxamide is the 4-toluenesulfonate salt and is a non-stoichiometric hydrate. Crystalline Form II of 2-{4-[(3S)-piperidin-3-yl]phenyl}-2H-indazole-7-carboxamide is also referred to by interchangeable terms such as: Form II of 2-{4-[(3S)-piperidin-3-yl]phenyl}-2H-indazole-7-carboxamide; crystalline Form II of niraparib; crystalline Form I; or Form II.

Figure 7:
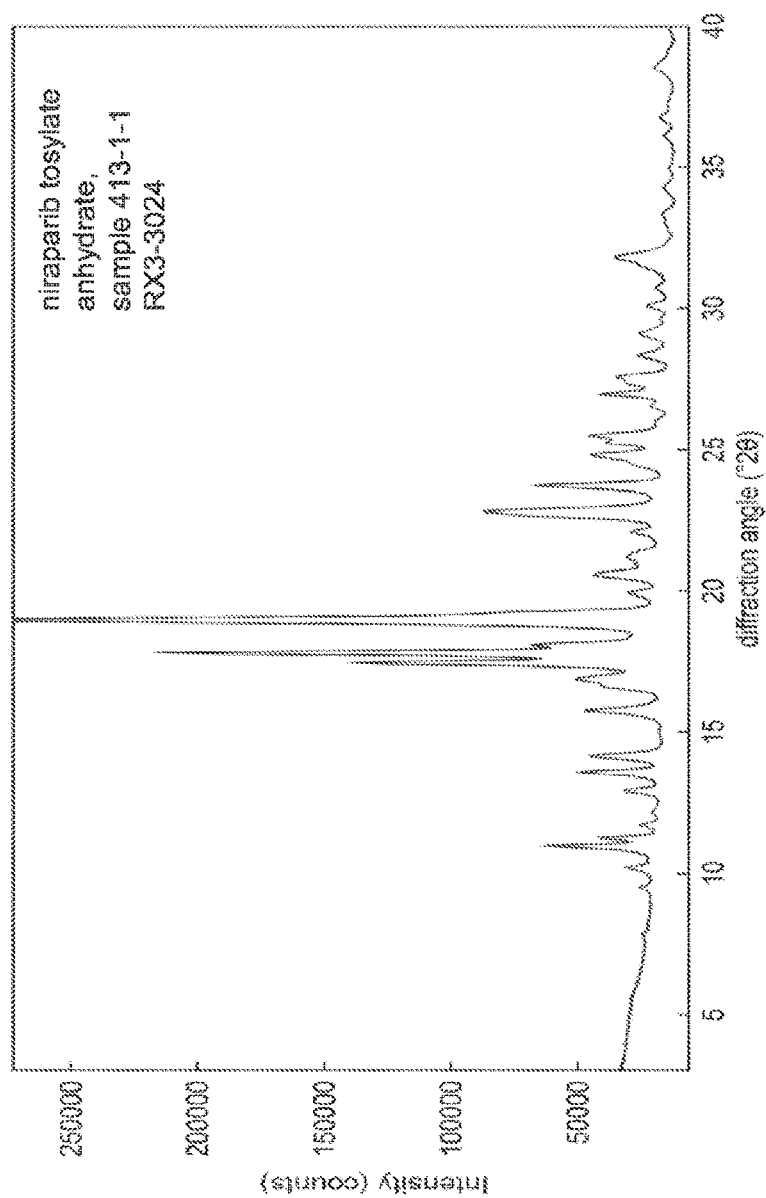
FIG. 7 shows an exemplary X-ray powder diffraction pattern for crystalline Form III of 2-{4-[(3S)-piperidin-3-yl]phenyl}-2H-indazole-7-carboxamide.
Figure 8:
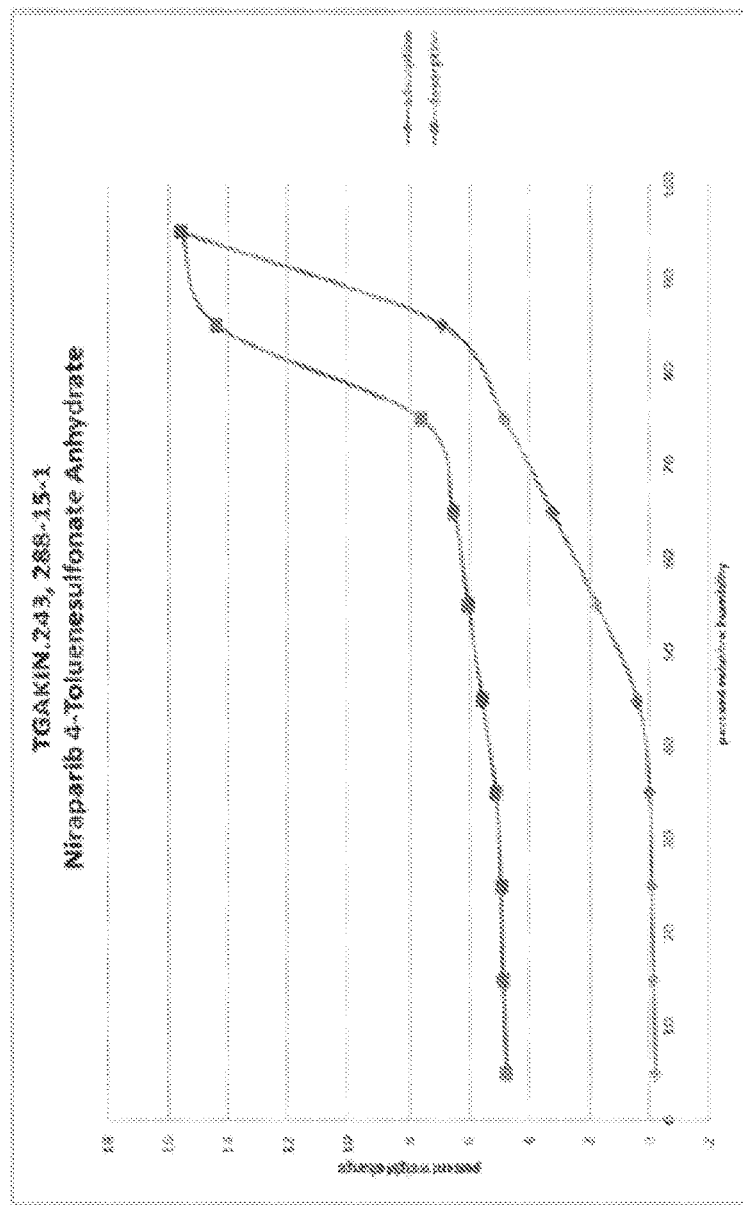
FIG. 8 shows an exemplary dynamic water vapor sorption pattern for crystalline anhydrous Form III of 2-{4-[(3S)-piperidin-3-yl]phenyl}-2H-indazole-7-carboxamide.

Provided herein is crystalline Form III of 2-{4-[(3S)-piperidin-3-yl]phenyl}-2H-indazole-7-carboxamide. Crystalline Form I of 2-{4-[(3S)-piperidin-3-yl]phenyl}-2H-indazole-7-carboxamide is the 4-toluenesulfonate salt and is an anhydrous form. Exemplary X-ray powder diffraction data for Form III is provided in FIG. 6 and FIG. 7. FIG. 2 shows an exemplary scanning differential calorimetry pattern for crystalline Form III of 2-{4-[(3S)-piperidin-3-yl]phenyl}-2H-indazole-7-carboxamide. FIG. 8 shows an exemplary dynamic water vapor sorption pattern for crystalline anhydrous Form III of 2-{4-[(3S)-piperidin-3-yl]phenyl}-2H-indazole-7-carboxamide. Crystalline Form fil of 2-{4-[(3S)-piperidin-3-yl]phenyl}-2H-indazole-7-carboxamide is also referred to by interchangeable terms such as: Form III of 2-{4-[(3S)-piperidin-3-yl]phenyl}-2H-indazole-7-carboxamide; crystalline anhydrous Form II of 2-{4-[(3S)-piperidin-3-yl]phenyl}-2H-indazole-7-carboxamide; crystalline Form III of niraparib; crystalline Form III; or Form III. FIG. 2 shows an exemplary scanning differential calorimetry pattern for crystalline Form II of 2-{4-[(3S)-piperidin-3-yl]phenyl}-2H-indazole-7-carboxamide Solid forms of 2-{4-[(3S)-piperidin-3-yl]phenyl}-2H-indazole-7-carboxamide described herein can have beneficial properties, including favorable properties for use in methods of treatment or in methods of manufacture of pharmaceutical formulations. For example, a hydrochloride salt of 2-{4-[(3S)-piperidin-3-yl]phenyl}-2H-indazole-7-carboxamide has been shown to be highly hygroscopic. By contrast, crystalline Form I of 2-{4-[(3S)-piperidin-3-yl]phenyl}-2H-indazole-7-carboxamide is a non-hygroscopic solid form having suitable solubility properties, as well as favorable physical and chemical stability.

One embodiment provides a composition comprising crystalline Form I of niraparib tosylate monohydrate substantially free of Form II and Form III. Another embodiment provides the composition wherein the crystalline Form I of niraparib tosylate monohydrate has an X-ray powder diffraction pattern substantially as shown in FIG. 1. Another embodiment provides the composition where the crystalline Form I of 2-{4-[(3S)-piperidin-3-yl]phenyl}-2H-indazole-7-carboxamide is characterized by at least one X-ray diffraction pattern reflection selected from a 2θ value of 9 5±0.2, 12.4±0.2, 13 2±0.2, 174±0.2, 18.4±0.2, 21.0±0.2, 24.9±0.2, 25.6±0.2, 26.0±0.2, and 26 9±0.2 Another embodiment provides the composition wherein the crystalline Form I of 2-{4-[(3S)-piperidin-3-yl]phenyl}-2H-indazole-7-carboxamide is characterized by an X-ray diffraction pattern reflection at 2θ=24.9±0.2. Another embodiment provides the composition wherein the crystalline Form I is characterized by X-ray diffraction pattern reflections at 2θ values of 9.5±0.2 and 26.0±0.2. Another embodiment provides the composition wherein the crystalline Form I is characterized by X-ray diffraction pattern reflections at a 2θ values of 12.4±0.2, 13.2±0 2, 17.4±0.2, 18.4±0.2, 21.0±0.2, 25.6±0.2, and 26.9±0.2. Another embodiment provides the composition wherein the crystalline Form I is characterized by at least one X-ray diffraction pattern reflection selected from a 2θ value of 12.4±0.2, 13.2±0.2, 17.4±0.2, 18.4±0.2, 21.0±0.2, 25.6±0.2, and 26.9±0.2. Another embodiment provides the composition wherein the crystalline Form I is characterized by at least two X-ray diffraction pattern reflections selected from a 2θ value of 12.4±0.2, 13.2±0.2, 17.4±0.2, 18.4±0.2, 21.0±0.2, 25.6±0.2, and 26.9±0.2. Another embodiment provides the composition wherein the crystalline Form I is characterized by at least three X-ray diffraction pattern reflections selected from a 2θ value of 12.4±0.2, 13.2±0.2, 17.4±0.2, 18.4±0.2, 21.0±0.2, 25.6±0.2, and 26.9±0.2. Another embodiment provides the composition wherein the crystalline Form I is characterized by at least four X-ray diffraction pattern reflections selected from a 2θ value of 12.4±0.2, 13.2±0.2, 17.4±0.2, 18.4±0.2, 21.0±0.2, 25.6±0.2, and 26.9±0.2. Another embodiment provides the composition wherein the crystalline Form I is characterized by a scanning differential calorimetry pattern substantially as shown in FIG. 2. Another embodiment provides the composition wherein the crystalline Form I is characterized by a Raman spectroscopy pattern substantially as shown in FIG. 3. Another embodiment provides the composition wherein the crystalline Form I is characterized by an infrared spectroscopy pattern substantially as shown in FIG. 4. Another embodiment provides the composition wherein the crystalline Form I is characterized by a dynamic water vapor sorption pattern substantially as shown in FIG. 5.

Figure 9:
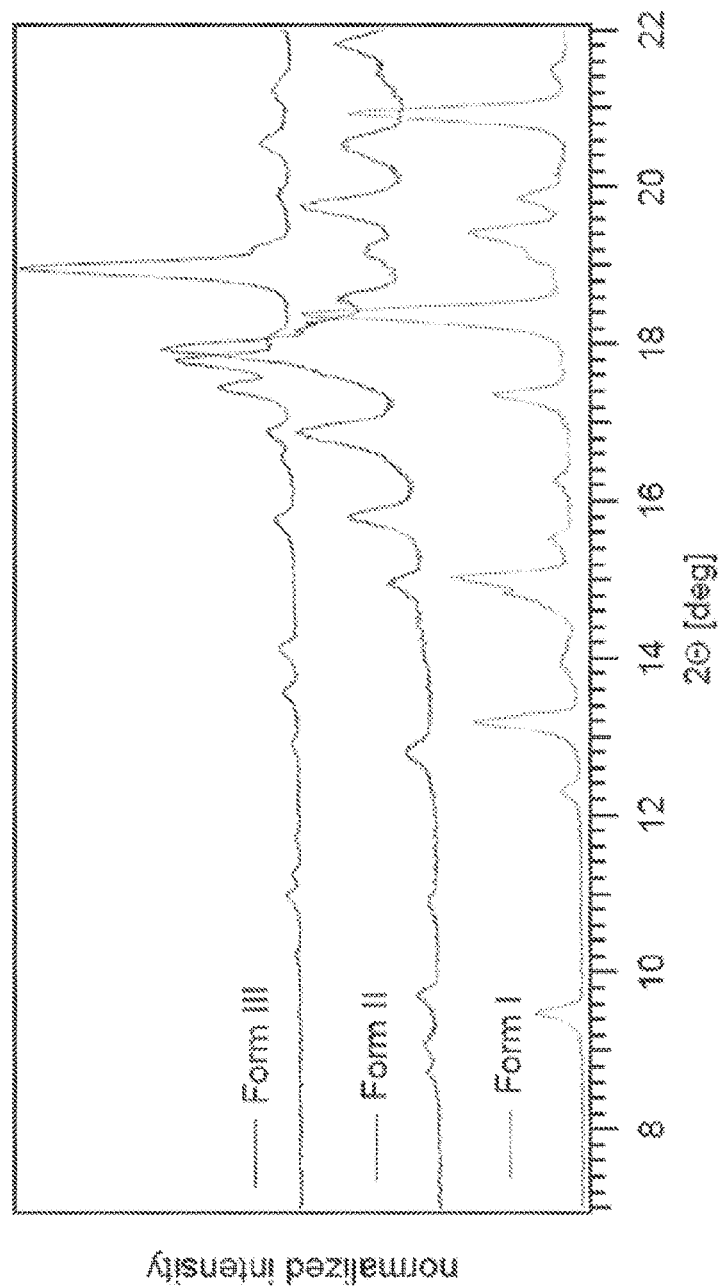
FIG. 9 shows an overlay of exemplary X-ray powder diffraction patterns for crystalline Form I, Form II and Form III of 2-{4-[(3S)-piperidin-3-yl]phenyl}-2H-indazole-7-carboxamide.

One embodiment provides a composition comprising crystalline Form II of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide and crystalline Form III of 2-{4-[(3S)-piperidin-3-yl]phenyl}-2H-indazole-7-carboxamide. One embodiment provides a composition comprising crystalline Form II of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide. One embodiment provides a composition comprising crystalline Form II 2-{4-[(3S)-piperidin-3-yl]phenyl}-2H-indazole-7-carboxamide and crystalline Form II of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide. In one embodiment, crystalline Form III is characterized by at least one X-ray diffraction pattern reflection selected from a 2θ value of 9.7±0.3, 12.8±0.3, 17.9±0.3, 19.7±0.3, and 21.8±0.3. In one embodiment, crystalline Form II has an X-ray powder diffraction pattern substantially as shown in FIG. 9 for Form II.

One embodiment provides a composition comprising crystalline Form III of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide and crystalline Form II of 2-{4-[(3S)-piperidin-3-yl]phenyl}-2H-indazole-7-carboxamide. One embodiment provides a composition comprising crystalline Form III of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide. One embodiment provides crystalline Form III characterized by at least one X-ray diffraction pattern reflection selected from a 2θ value of 17.8±0.2, 19.0±0.2, or 22.8±0.2. One embodiment provides crystalline Form III that has an X-ray powder diffraction pattern substantially as shown in FIG. 9 for Form III. One embodiment provides crystalline Form III of 2-{4-[(3S)-piperidin-3-yl]phenyl}-2H-indazole-7-carboxamide that has an X-ray powder diffraction pattern substantially as shown in FIG. 7. One embodiment provides crystalline Form III of 2-{4-[(3S)-piperidin-3-yl]phenyl}-2H-indazole-7-carboxamide characterized by a dynamic water vapor sorption pattern substantially as shown in FIG. 8. One embodiment provides crystalline Form III of 2-{4-[(3S)-piperidin-3-yl]phenyl}-2H-indazole-7-carboxamide characterized by a scanning differential calorimetry pattern substantially as shown in FIG. 2.

Niraparib is a selective poly(ADP-ribose) polymerase (PARP) 1 and 2 inhibitor which selectively kills tumor cells in vitro and in mouse xenograft models PARP inhibition leads to irreparable double strand breaks (DSBs), use of the error-prone DNA repair pathway, resultant genomic instability, and ultimately cell death. Additionally, PARP trapped at genetic lesions as a result of the suppression of autoparlyation can contribute to cytotoxicity.

ZEJULA™ is indicated for the maintenance or treatment of adult patients with recurrent epithelial ovarian, fallopian tube, or primary peritoneal cancer following a complete or partial response to platinum-based chemotherapy. Each ZEJULA™ capsule contains 100 mg of niraparib (as tosylate monohydrate). The hard capsules have a white body with "100 mg" printed in black ink, and a purple cap with "Niraparib" printed in white ink. The recommended dose of ZEJULA™ as monotherapy is three 100 mg capsules taken orally once daily, equivalent to a total daily dose of 300 mg.

Provided herein is an oral composition containing niraparib or its pharmaceutically acceptable salts. In some embodiments, the oral composition includes from about 20 wt % to about 60 wt % of niraparib for treatment of a disorder or condition such as cancer; and a pharmaceutically acceptable carrier, wherein the niraparib is distributed with substantial uniformity throughout the pharmaceutically acceptable carrier.

In some embodiments, the disorder or condition is cancer, for example, ovarian cancer.

In some embodiments, the niraparib is a pharmaceutically acceptable salt thereof. In some embodiments, the pharmaceutically acceptable salt is niraparib tosylate monohydrate.

In some embodiments, the niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1.

In some embodiments, the pharmaceutical composition comprises about 50 mg to about 300 mg of niraparib tosylate monohydrate. In some embodiments, the pharmaceutical composition comprises about 50 mg to about 300 mg of niraparib tosylate monohydrate as a crystalline Form I substantially free of Form II and Form III. Another embodiment provides the composition wherein the crystalline Form I of niraparib tosylate monohydrate has an X-ray powder diffraction pattern substantially as shown in FIG. 1.

For example, the pharmaceutical composition can comprise about 100 mg to about 200 mg of niraparib tosylate monohydrate. For example, the pharmaceutical composition can comprise about 125 mg to about 175 mg of niraparib tosylate monohydrate.

The formulation can comprise one or more components, including niraparib. The components can be combined to create a powder blend that is used to fill capsules. For example, the powder blend can be filled into gelatin capsules, such as size 0 gelatin capsules.

The niraparib may be present in the formulation as a pharmaceutically acceptable salt. For example, the niraparib can be niraparib tosylate monohydrate.

The formulation can comprise one or more diluents. For example, the formulation can comprise lactose monohydrate.

The formulation can comprise one or more lubricants. For example, For example, the formulation can comprise magnesium stearate.

An exemplary niraparib formulation of the present invention comprises 100 mg of niraparib (based on free base, 1.000 mg niraparib anhydrous free base is equivalent to 1.594 mg niraparib tosylate monohydrate), 254.5 mg of lactose monohydrate and magnesium stearate. An exemplary niraparib formulation of the present invention comprises 100 mg of niraparib (based on free base, 1.000 mg niraparib anhydrous free base is equivalent to 1.594 mg niraparib tosylate monohydrate), 254.5 mg of lactose monohydrate, and magnesium stearate. It may also optionally comprise tartrazine.

Niraparib Concentration/Amount

By means of methods and compositions described herein, formulations can be made that achieve therapeutically effective pharmacokinetic profiles. For example, therapeutically effective doses of niraparib can be administered once, twice or three times daily in capsules using the manufacturing methods and compositions that have been described herein to achieve these results. In some embodiments, the niraparib is present in an amount of from about 20-80 wt %, about 45-70 wt %, about 40-50 wt %, about 45-55 wt %, about 50-60 wt %, about 55-65 wt %, about 60-70 wt %, about 65-75 wt %, about 70-80 wt %, or about 40-60 wt %. In some embodiments, the niraparib is niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1.

In some embodiments, the compositions described herein have a concentration of niraparib of from about 1% to about 50%, from about 5% to about 50%, from about 10% to about 50%, from about 15% to about 50%, from about 20%, to about 50%, from about 25% to about 50%, from about 30% to about 50%, from about 35% to about 50%, from about 40% to about 50%, or from about 45% to about 50%, by weight of the composition. In some embodiments, the niraparib is niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1.

In some embodiments, the compositions described herein have a concentration of niraparib of from about 1% to about 45%, from about 5% to about 45%, from about 10% to about 45%, from about 15% to about 45%, from about 20% to about 45%, from about 25% to about 45%, from about 30% to about 45%, from about 35% to about 45%, or from about 40% to about 45% by weight of the composition. In some embodiments, the niraparib is niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1.

In some embodiments, the compositions described herein have a concentration of niraparib of from about 1% to about 40%, from about 5% to about 40%, from about 10% to about 40%, from about 15% to about 40%, from about 20% to about 40%, from about 25% to about 40%, from about 30% to about 40%, from about 35% to about 40% by weight of the composition. In some embodiments, the niraparib is niraparib tosylate monohydrate is a crystalline Form I substantially free of Form I and Form III. Another embodiment provides the composition wherein the crystalline Form I of niraparib tosylate monohydrate has an X-ray powder diffraction pattern substantially as shown in FIG. 1.

In some embodiments, the compositions described herein have a concentration of niraparib of from about 1% to about 35%, from about 5% to about 35%, from about 10% to about 35%, from about 15% to about 35%, from about 20% to about 35%, from about 25% to about 35%, or from about 30% to about 35% by weight of the composition. In some embodiments, the niraparib is niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1.

In some embodiments, the compositions described herein have a concentration of niraparib of about 1%, 5%, 10%, 15%, 20%, 25%, 30%, 35%, 40%, 45%, or 50% by weight of the composition. In some embodiments, the compositions described herein have a concentration of niraparib tosylate monohydrate of about 19.16% by weight of the composition. In some embodiments, the compositions described herein have a concentration of niraparib tosylate monohydrate of about 38.32% by weight of the composition. In some embodiments, the compositions described herein have a concentration of niraparib tosylate monohydrate of about 57.48% by weight of the composition. In some embodiments, the compositions described herein have a concentration of niraparib tosylate monohydrate of about 76.64% by weight of the composition. In some embodiments, the niraparib is niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1.

In some embodiments, the compositions described herein have an amount of niraparib of from about 1 mg to 5 mg, 5 mg to 10 mg, 10 mg to 20 mg, 20 mg to 25 mg, 25 mg to 50 mg, 50 mg to 75 mg, 70 ng to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg. In some embodiments, the niraparib is niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1. For example, the compositions described herein can have an amount of niraparib tosylate monohydrate of from about 1 mg to about 1000 mg, for example, from about 1 mg to 5 mg, 5 mg to 10 mg, 10 mg to 20 mg, 20 mg to 25 mg, 25 mg to 50 mg, 50 mg to 75 mg, 70 ng to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg.

In some embodiments, the compositions described herein have an amount of niraparib of about 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, or 1000 mg. In some embodiments, the niraparib is niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1. For example, the compositions described herein can have an amount of niraparib tosylate monohydrate of about 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, or 1000 mg.

In some embodiments, the compositions described herein have an amount of niraparib of about 25 mg, about 50 mg, about 100 mg, about 150 mg, about 200 mg, about 250 mg, about 300 mg, about 350 mg, about 400 mg, about 450 mg, or about 500 mg. For example, the compositions described herein can have an amount of niraparib tosylate monohydrate of about 25 mg, about 50 mg, about 100 mg, about 150 mg, about 200 mg, about 250 mg, about 300 mg, about 350 mg, about 400 mg, about 450 mg, or about 500 mg. In some embodiments, the compositions described herein have an amount of niraparib tosylate monohydrate of about 79.7 mg. In some embodiments, the compositions described herein have an amount of niraparib tosylate monohydrate of about 159.4 mg. In some embodiments, the compositions described herein have an amount of niraparib tosylate monohydrate of about 159.4 mg, wherein the niraparib is niraparib tosylate monohydrate is a crystalline Form I substantially free of Form II and Form III. In some embodiments, the compositions described herein have an amount of niraparib tosylate monohydrate of about 159.4 mg, wherein the niraparib is niraparib tosylate monohydrate is a crystalline Form I substantially free of Form II and Form III In some embodiments, the compositions described herein have an amount of niraparib tosylate monohydrate of about 159.4 mg, wherein the niraparib tosylate monohydrate is the crystalline Form I with an X-ray powder diffraction pattern substantially as shown in FIG. 1. In some embodiments, the compositions described herein have an amount of niraparib tosylate monohydrate of about 318.8 mg. In some embodiments, the compositions described herein have an amount of niraparib tosylate monohydrate of about 478.2 mg. In some embodiments, the niraparib is niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1.

Pharmaceutically Acceptable Excipients

In some aspects, the pharmaceutical composition disclosed herein comprises one or more pharmaceutically acceptable excipients. Exemplary pharmaceutically acceptable excipients for the purposes of pharmaceutical compositions disclosed herein include, but are not limited to, binders, disintegrants, superdisintegrants, lubricants, diluents, fillers, flavors, glidants, sorbents, solubilizers, chelating agents, emulsifiers, thickening agents, dispersants, stabilizers, suspending agents, adsorbents, granulating agents, preservatives, buffers, coloring agents and sweeteners or combinations thereof. Examples of binders include microcrystalline cellulose, hydroxypropyl methylcellulose, carboxyvinyl polymer, polyvinylpyrrolidone, polyvinylpolypyrrolidone, carboxymethylcellulose calcium, carboxymethylcellulose sodium, ceratonia, chitosan, cottonseed oil, dextrates, dextrin, ethylcellulose, gelatin, glucose, glyceryl behenate, galactomannan polysaccharide, hydroxyethyl cellulose, hydroxyethylmethyl cellulose, hydroxypropyl cellulose, hypromellose, inulin, lactose, magnesium aluminum silicate, maltodextrin, methylcellulose, poloxamer, polycarbophil, polydextrose, polyethylene glycol, polyethylene oxide, polymethacrylates, sodium alginate, sorbitol, starch, sucrose, sunflower oil, vegetable oil, tocofersolan, zein, or combinations thereof. Examples of disintegrants include hydroxypropyl methylcellulose (HPMC), low substituted hydroxypropyl cellulose (L-HPC), croscarmellose sodium, sodium starch glycolate, lactose, magnesium aluminum silicate, methylcellulose, polacrilin potassium, sodium alginate, starch, or combinations thereof. Examples of a lubricant include stearic acid, sodium stearyl fumarate, glyceryl behenate, calcium stearate, glycerin monostearate, glyceryl palmitostearate, magnesium lauryl sulfate, mineral oil, palmitic acid, myristic acid, poloxamer, polyethylene glycol, sodium benzoate, sodium chloride, sodium lauryl sulfate, talc, zinc stearate, potassium benzoate, magnesium stearate or combinations thereof. Examples of diluents include talc, ammonium alginate, calcium carbonate, calcium lactate, calcium phosphate, calcium silicate, calcium sulfate, cellulose, cellulose acetate, corn starch, dextrates, dextrin, dextrose, erythritol, ethylcellulose, fructose, fumaric acid, glyceryl palmitostearate, isomalt, kaolin, lactitol, lactose, magnesium carbonate, magnesium oxide, maltodextrin, maltose, mannitol, microcrystalline cellulose, polydextrose, polymethacrylates, simethicone, sodium alginate, sodium chloride, sorbitol, starch, sucrose, sulfobutylether β-cyclodextrin, tragacanth, trehalose, xylitol, or combinations thereof. In some embodiments, the pharmaceutically acceptable excipient is hydroxypropyl methylcellulose (HPMC). In some embodiments, the pharmaceutically acceptable excipient is low substituted hydroxypropyl cellulose (L-HPC). In some embodiments, the pharmaceutically acceptable excipient is lactose. In some embodiments, the pharmaceutically acceptable excipient is lactose monohydrate. In some embodiments, the pharmaceutically acceptable excipient is magnesium stearate. In some embodiments, the pharmaceutically acceptable excipient is lactose monohydrate and magnesium stearate.

Various useful fillers or diluents include, but are not limited to calcium carbonate (Barcroft™, MagGran™, MLillicarb™, Pharma-Carb™, Precarb™, Sturcal™, Vivapres Ca™), calcium phosphate, dibasic anhydrous (Emcompress Anhydrous™, Fujicalin™), calcium phosphate, dibasic dihydrate (Calstar™, Di-Cafos™, Emcompress™), calcium phosphate tribasic (Tri-Cafos™, TRI-TAB™), calcium sulphate (Destab™, Drierite™, Snow White™, Cal-Tab™, Compactrol™), cellulose powdered (Arbocel™, Elcema™, Sanacet™), silicified microcrystailine cellulose, cellulose acetate, compressible sugar (Di-Pac™), confectioner's sugar, dextrates (Candex™, Emdex™), dextrin (Avedex™, Caloreen™, Primogran W™), dextrose (Caridex™, Dextrofin™, Tab fine D-IOO™), fructose (Fructofin™, Krystar™), kaolin (Lion™, Sim 90™), lactitol (Finlac DC™, Finlac MCX™), lactose (Anhydrox™, CapsuLac™, Fast-FloT™, FlowLac™, GranuLac™, inhaLac™, Lactochem™, Lactohaie™, Lactopress™, Microfme™, Microtose™, Pharmatose™, Prisma Lac™, Respitose™, SacheLac™, SorboLac™, Super-Tab™, Tablettose™, Wyndale™, Zeparox™), lactose monohydrate, magnesium carbonate, magnesium oxide (MagGran MO™), maltodextrin (C*Dry MD™, Lycatab DSH™, Maldex™, Maitagran™, Maltrin™, Maltrin QD™, Paselli MD 10 PH™, Star-Dri™), maltose (Advantose 100™), mannitol (Mannogem™, Pearlitol™), microcrystalline cellulose (Avicel PH™, Celex™, Celpherem, Ceolus KG™, Emcocel™, Pharmacel™, Tabulose™, Vivapur™), polydextrose (Litesse™), simethicone (Dow Corning Q7-2243 LVA™, Cow Coming Q7-2587™, Sentry Simethicone™), sodium alginate (Keltone™, Protanal™), sodium chloride (Alberger™), sorbitol (Liponec 70-NC™, Liponic 76-NCv, Meritol™, Neosorb™, Sorbitol Instant™, Sorbogem™), starch (Flufiex W™, Instant Pure-Cote™, Melojej™, Meritena Paygel 55™, Perfectamyl D6PH™, Pure-Cote™, Pure-Dent™, Pure-Gel™, Pure-Set™, Purity 21™, Purity 826™, Tablet White™), pregelatinized starch, sucrose, trehalose and xylitol, or mixtures thereof.

In some embodiments, a filler such as lactose monohydrate is present in an amount of about 5-90% by weight. In some embodiments, a filler such as lactose monohydrate is present in an amount of about 5-80% by weight. In some embodiments, a filler such as lactose monohydrate is present in an amount of about 5-70% by weight. In some embodiments, a filler such as lactose monohydrate is present in an amount of about 5-60% by weight. In some embodiments, a filler such as lactose monohydrate is present in an amount of about 5-50% by weight. In some embodiments, a filler such as lactose monohydrate is present in an amount of about 5-40% by weight. In some embodiments, a filler such as lactose monohydrate is present in an amount of about 5-30% by weight. In some embodiments, a filler such as lactose monohydrate is present in an amount of about 25-90% by weight. In some embodiments, a filler such as lactose monohydrate is present in an amount of about 25-80% by weight. In some embodiments, a filler such as lactose monohydrate is present in an amount of about 25-70% by weight. In some embodiments, a filler such as lactose monohydrate is present in an amount of about 25-60% by weight. In some embodiments, a filler such as lactose monohydrate is present in an amount of about 25-50% by weight. In some embodiments, a filler such as lactose monohydrate is present in an amount of about 25-40% by weight. In some embodiments, a filler such as lactose monohydrate is present in an amount of about 40-90% by weight. In some embodiments, a filler such as lactose monohydrate is present in an amount of about 40-800% by weight. In some embodiments, a tiller such as lactose monohydrate is present in an amount of about 40-70% by weight. In some embodiments, a filler such as lactose monohydrate is present in an amount of about 40-60% by weight. In some embodiments, a filler such as lactose monohydrate is present in an amount of about 40-50% by weight. In some embodiments, a filler such as lactose monohydrate is present in an amount of about 40% by weight. In some embodiments, a filler such as lactose monohydrate is present in an amount of about 50% by weight. In some embodiments, a filler such as lactose monohydrate is present in an amount of about 60% by weight. In some embodiments, a filler such as lactose monohydrate is present in an amount of about 70% by weight. In some embodiments, a filler such as lactose monohydrate is present in an amount of about 80% by weight.

In some embodiments, a filler such as lactose monohydrate is present in an amount of from about 25 mg to about 1000 mg, from about 50 mg to about 1000 mg, from about 100 mg to about 1000 mg, from about 150 mg to about 1000 mg, from about 200 mg to about 1000 mg, from about 250 mg to about 1000 mg, from about 300 mg to about 1000 mg, from about 350 mg to about 1000 mg, from about 400 mg to about 1000 mg, from about 450 mg to about 1000 mg, or from about 500 mg to about 1000 mg. For example, a filler such as lactose monohydrate can be present in an amount of from about 25 mg to about 1000 mg, from about 50 mg to about 1000 mg, from about 100 mg to about 1000 mg, from about 150 mg to about 1000 mg, from about 200 mg to about 1000 mg, from about 250 mg to about 1000 mg, from about 300 mg to about 1000 mg, from about 350 mg to about 1000 mg, from about 400 mg to about 1000 mg, from about 450 mg to about 1000 mg, or from about 500 mg to about 1000 mg.

In some embodiments, a filler such as lactose monohydrate is present in an amount of from about 25 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, or from about 500 mg to about 550 mg. For example, a filler such as lactose monohydrate can be present in an amount of from about 25 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, or from about 500 mg to about 550 mg.

In some embodiments, a filler such as lactose monohydrate is present in an amount of about 15 mg, about 25 mg, about 50 mg, about 100 mg, about 150 mg, about 200 mg, about 250 mg, about 300 mg, about 350 mg, about 400 mg, about 450 mg, or about 500 mg. For example, a filler such as lactose monohydrate is present in an amount of about 15 mg, about 25 mg, about 50 mg, about 100 mg, about 150 mg, about 200 mg, about 250 mg, about 300 mg, about 350 mg, about 400 mg, about 450 mg, or about 500 mg. In some embodiments, a filler such as lactose monohydrate is present in an amount of about 334.2 mg. In some embodiments, a filler such as lactose monohydrate is present in an amount of about 254.5 mg. In some embodiments, a filler such as lactose monohydrate is present in an amount of about 174.8 mg. In some embodiments, a filler such as lactose monohydrate is present in an amount of about 95.1 mg. In some embodiments, a filler such as lactose monohydrate is present in an amount of about 15.4 mg.

Various useful disintegrants include, but are not limited to, alginic acid (Protacid™, Satialgine H8™), calcium phosphate, tribasic (TRI-TAB™), carboxymethylcellulose calcium (ECG 505™), carboxymethylcellulose sodium (Akucell™, Finnfix™, Nymcel Tylose CB™), colloidal silicon dioxide (Aerosil™, Cab-O-Sil™, Wacker HDK™), croscarmellose sodium (Ac-Di-Sol™, Pharmacel XL™, Primellose™, Solutab™, Vivasol™), crospovidone (Collison CL™, Collison CL-M™, Polyplasdone XL™), docusate sodium, guar gum (Meyprodor™, Meyprofm™, Meyproguar™), low substituted hydroxypropyl cellulose, magnesium aluminum silicate (Magnabite™, Neusilin™, Pharmsorb™, Veegum™), methylcellulose (Methocel™, Metolose™), microcrystalline cellulose (Avicel PH™, Ceoius KG™, Emcoel™, Ethispheres™, Fibrocel™, Pharmacel™, Vivapur™), povidone (Collison™, Plasdone™) sodium alginate (Kelcosol™, Ketone™, Protanal™), sodium starch glycolate, polacrilin potassium (Amberlite IRP887™), silicified microcrystalline cellulose (ProSotv™), starch (Aytex P™, Fluftex W™, Melojel™, Meritena™, Paygel 55™, Perfectamyl D6PH™, Pure-Bind™, Pure-Cote™, Pure-Dent™, Purity 21™, Purity 826™, Tablet White™) or pre-gelatinized starch (Lycatab PGS™, Merigel™, National 78-155™, Pharma-Gel™, Prejel™, Sepistab ST 200™, Spress B820™, Starch 1500 G™, Tablitz™, Unipure LD™), or mixtures thereof. In some embodiments, a disintegrant is optionally used in an amount of about 0-10% by weight. In some embodiments, a disintegrant is present in an amount of from about 0.1 mg to 0.5 mg, 0.5 mg to 1 mg, 1 mg to 2 mg, 2 mg to 2.5 mg, 2.5 mg to 5 mg, 5 mg to 7.5 mg, 7 mg to 9.5 mg, 9 mg to 11.5 mg, 11 mg to 13.5 mg, 13 mg to 15.5 mg, 15 mg to 17.5 mg, 17 to 19.5 mg, 19 mg to 21.5 mg, 21 mg to 23.5 mg, 23 mg to 25.5 mg, 25 mg to 27.5 mg, 27 mg to 30 mg, 29 mg to 31.5 mg, 31 mg to 33.5 mg, 33 mg to 35.5 mg, 35 mg to 37.5 mg, 37 mg to 40 mg, 40 mg to 45 mg, 45 mg to 50 mg, 50 mg to 55 mg, 55 mg to 60 mg, 60 mg to 65 mg, 65 mg to 70 mg, 70 mg to 75 mg, 75 mg to 80 mg, 80 mg to 85 mg, 85 mg to 90 mg, 90 mg to 95 mg, or 95 mg to 100 mg. In some embodiments, a disintegrant is present in an amount of about 0.1 mg, 0.5 mg, 1 mg, 2 mg, 2.5 mg, 5 mg, 7 mg, 9 mg, 11 mg, 13 mg, 15 mg, 17 mg, 19 mg, 21 mg, 23 mg, 25 mg, 27.5 mg, 30 mg, 31.5 mg, 33.5 mg, 35.5 mg, 37.5 mg, 40 mg, 45 mg, 50 mg, 55 mg, 60 mg, 65 mg, 70 mg, 75 mg, 80 mg, 85 mg, 90 mg, 95 mg, or 100 mg.

Various useful lubricants include, but are not limited to, calcium stearate (HyQual™), glycerine monostearate (Imwitor™ 191 and 900, Kessco GMS5™, 450 and 600, Myvaplex 600P™, Myvatex™, Rita GMS™, Stepan GMS™, Tegin™, Tegin™ 503 and 515, Tegin 4100™, Tegin M™, Unimate GMS™), glyceryl behenate (Compritol 888 ATO™), glyceryl palmitostearate (Precirol ATO 5™), hydrogenated castor oil (Castorwax MP 80™, Croduret™, Cutina HR™, Fancol™, Simulsol 1293™), hydrogenated vegetable oil 0 type I (Sterotex™, Dynasan P60™, Hydrocote™, Lipovol HS-K™, Sterotex HM™), magnesium lauryl sulphate, magnesium stearate, medium-chain triglycerides (Captex 300™, Labrafac CC™, Miglyol 810™, Neobee M5™, Nesatol™, Waglinol 3/9280™), poloxamer (Pluronic™, Synperonic™), polyethylene 5 glycol (Carbowax Sentry™, Lipo™, Lipoxol™, Lutrol E™, Pluriol E™), sodium benzoate (Antimol™), sodium chloride, sodium lauryl sulphate (Elfan 240™, Texapon KI 2P™), sodium stearyl fumarate (Pruv™), stearic acid (Hystrene™, Industrene™, Kortacid 1895™, Pristerene™), talc (Altaic™, Luzenac™, Luzenac Pharma™, Magsil Osmanthus™, 0 Magsil Star™, Superiore™), sucrose stearate (Surfhope SE Pharma D-1803 F™) and zinc stearate (HyQual™) or mixtures thereof. Examples of suitable lubricants include, but are not limited to, magnesium stearate, calcium stearate, zinc stearate, stearic acid, talc, glyceryl behenate, polyethylene glycol, polyethylene oxide polymers, sodium lauryl sulfate, magnesium lauryl sulfate, sodium oleate, sodium stearyl fumarate, DL-leucine, colloidal silica, and others as known in the art. In some embodiments a lubricant is magnesium stearate.

In some embodiments, a lubricant such as magnesium stearate is present in an amount of about 0.1-5% by weight. In some embodiments, a lubricant such as magnesium stearate is present in an amount of about 0.1-2% by weight. In some embodiments, a lubricant such as magnesium stearate is present in an amount of about 0.1-1% by weight. In some embodiments, a lubricant such as magnesium stearate is present in an amount of about 0.1-0.75% by weight. In some embodiments, a lubricant such as magnesium stearate is present in an amount of about 0.1-5% by weight. In some embodiments, a lubricant such as magnesium stearate is present in an amount of about 0.2-5% by weight. In some embodiments, a lubricant such as magnesium stearate is present in an amount of about 0.2-2% by weight. In some embodiments, a lubricant such as magnesium stearate is present in an amount of about 0.2-1% by weight. In some embodiments, a lubricant such as magnesium stearate is present in an amount of about 0.2-0.75% by weight. In some embodiments, a lubricant such as magnesium stearate is present in an amount of about 0.3% by weight. In some embodiments, a lubricant such as magnesium stearate is present in an amount of about 0.4% by weight. In some embodiments, a lubricant such as magnesium stearate is present in an amount of about 0.5% by weight. In some embodiments, a lubricant such as magnesium stearate is present in an amount of about 0.6% by weight. In some embodiments, a lubricant such as magnesium stearate is present in an amount of about 0.7% by weight. In some embodiments, a lubricant is present in an amount of from about 0.01 mg to 0.05 mg, 0.05 mg to 0.1 mg, 0.1 mg to 0.2 mg, 0.2 mg to 0.25 mg, 0.25 mg to 0.5 mg, 0.5 mg to 0.75 mg, 0.7 mg to 0.95 mg, 0.9 mg to 1.15 mg, 1.1 mg to 1.35 mg, 1.3 mg to 1.5 mg, 1.5 mg to 1.75 mg, 1.75 to 1.95 mg, 1.9 mg to 2.15 mg, 2.1 mg to 2.35 mg, 2.3 mg to 2.55 mg, 2.5 mg to 2.75 mg, 2.7 mg to 3.0 mg, 2.9 mg to 3.15 mg, 3.1 mg to 3.35 mg, 3.3 mg to 3.5 mg, 3.5 mg to 3.75 mg, 3.7 mg to 4.0 mg, 4.0 mg to 4.5 mg, 4.5 mg to 5.0 mg, 5.0 mg to 5.5 mg, 5.5 mg to 6.0 mg, 6.0 mg to 6.5 mg, 6.5 mg to 7.0 mg, 7.0 mg to 7.5 mg, 7.5 mg to 8.0 mg, 80 mg to 8.5 mg, 8.5 mg to 9.0 mg, 9.0 mg to 9.5 mg, or 9.5 mg to 10.0 mg. In some embodiments, a lubricant is present in an amount of about 0.01 mg, 0.05 mg, 0.1 mg, 0.2 mg, 0.25 mg, 0.5 mg, 0.7 mg, 0.9 mg, 11 mg, 1.3 mg, 1.5 mg, 1.7 mg, 1.9 mg, 2. mg, 2.3 mg, 2.5 mg, 2.75 mg, 3.0 mg, 3.1 mg, 3.3 mg, 3.5 mg, 3.7 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg, or 10.0 mg.

Various useful glidants include, but are not limited to, tribasic calcium phosphate (TRI-TAB™), calcium silicate, cellulose, powdered (Sanacel™, Solka-Floe™), colloidal silicon dioxide (Aerosil™, Cab-O-Sil M-5P™, Wacker HDK™), magnesium silicate, magnesium trisilicate, starch (Melojel™, Meritena™, Paygel 55™, Perfectamyl D6PH™, Pure-Bind™, Pure-Cote™, Pure-Dent™, Pure-Gel™, Pure-Set™, Purity 21™, Purity 826™, Tablet White™) and talc (Luzenac Pharma™, Magsil Osmanthus™, Magsil Star™, Superiore™), or mixtures thereof. In some embodiments, a glidant is optionally used in an amount of about 0-15% by weight. In some embodiments, a glidant is present in an amount of from about 0.1 mg to 0.5 mg, 0.5 mg to 1 mg, 1 mg to 2 mg, 2 mg to 2.5 mg, 2.5 mg to 5 mg, 5 mg to 7.5 mg, 7 mg to 9.5 mg, 9 mg to 11.5 mg, 11 mg to 13.5 mg, 13 mg to 15.5 mg, 15 mg to 17.5 mg, 17 to 19.5 mg, 19 mg to 21.5 mg, 21 mg to 23.5 mg, 23 mg to 25.5 mg, 25 mg to 27.5 mg, 27 mg to 30 mg, 29 mg to 31.5 mg, 31 mg to 33.5 mg, 33 mg to 35.5 mg, 35 mg to 37.5 mg, 37 mg to 40 mg, 40 mg to 45 mg, 45 mg to 50 mg, 50 mg to 55 mg, 55 mg to 60 mg, 60 mg to 65 mg, 65 mg to 70 mg, 70 mg to 75 mg, 75 mg to 80 mg, 80 mg to 85 mg, 85 mg to 90 mg, 90 mg to 95 mg, or 95 mg to 100 mg. In some embodiments, a glidant is present in an amount of about 0.1 mg, 0.5 mg, 1 mg, 2 mg, 2.5 mg, 5 mg, 7 mg, 9 mg, 11 mg, 13 mg, 15 mg, 17 mg, 19 mg, 21 mg, 23 mg, 25 mg, 27.5 mg, 30 mg, 31.5 mg, 33.5 mg, 35.5 mg, 37.5 mg, 40 mg, 45 mg, 50 mg, 55 mg, 60 mg, 65 mg, 70 mg, 75 mg, 80 mg, 85 mg, 90 mg, 95 mg, or 100 mg.

Pharmaceutically acceptable surfactants include, but are limited to both non-ionic and ionic surfactants suitable for use in pharmaceutical dosage forms. Ionic surfactants may include one or more of anionic, cationic or zwitterionic surfactants. Various useful surfactants include, but are not limited to, sodium lauryl sulfate, monooleate, monolaurate, monopalmitate, monostearate or another ester of olyoxyethylene sorbitane, sodium dioctylsulfosuccinate (DOSS), lecithin, stearyic alcohol, cetostearylic alcohol, cholesterol, polyoxyethylene ricin oil, polyoxyethylene fatty acid glycerides, poloxamer, or any other commercially available co-processed surfactant like SEPITRAP® 80 or SEPI-TRAP® 4000 and mixtures thereof. In some embodiments, surfactant is optionally used in an amount of about 0-5% by weight. In some embodiments, a surfactant is present in an amount of from about 0.1 mg to 0.5 mg, 0.5 mg to 1 mg, 1 mg to 2 mg, 2 mg to 2.5 mg, 2.5 mg to 5 mg, 5 mg to 7.5 mg, 7 mg to 9.5 mg, 9 mg to 11.5 mg, 11 mg to 13.5 mg, 13 mg to 15.5 mg, 15 mg to 17.5 mg, 17 to 19.5 mg, 19 mg to 21.5 mg, 21 mg to 23.5 mg, 23 mg to 25.5 mg, 25 mg to 27.5 mg, 27 mg to 30 mg, 29 mg to 31.5 mg, 31 mg to 33.5 mg, 33 mg to 35.5 mg, 35 mg to 37.5 mg, 37 mg to 40 mg, 40 mg to 45 mg, 45 mg to 50 mg, 50 mg to 55 mg, 55 mg to 60 mg, 60 mg to 65 mg, 65 mg to 70 mg, 70 mg to 75 mg, 75 mg to 80 mg, 80 mg to 85 mg, 85 mg to 90 mg, 90 mg to 95 mg, or 95 mg to 100 mg. In some embodiments, a surfactant is present in an amount of about 0.1 mg, 0.5 mg, 1 mg, 2 mg, 2.5 mg, 5 mg, 7 mg, 9 mg, 11 mg, 13 mg, 15 mg, 17 mg, 19 mg, 21 mg, 23 mg, 25 mg, 27.5 mg, 30 mg, 31.5 mg, 33.5 mg, 35.5 mg, 37.5 mg, 40 mg, 45 mg, 50 mg, 55 mg, 60 mg, 65 mg, 70 mg, 75 mg, 80 mg, 85 mg, 90 mg, 95 mg, or 100 mg.

Stability

In some embodiments, the pharmaceutical composition disclosed herein is stable for at least about: 30 days, 60 days, 90 days, 6 months, 1 year, 18 months, 2 years, 3 years, 4 years, or 5 years, for example about 80%-100% such as about: 80%, 90%, 95%, or 100% of the active pharmaceutical agent in the pharmaceutical composition is stable, e.g., as measured by High Performance Liquid Chromatography (HPLC). In some embodiments, about 80%-100% (e.g., about: 90%-100% or 95-100%) of niraparib or a pharmaceutically acceptable salt thereof (e.g., niraparib tosylate monohydrate) in the pharmaceutical composition disclosed herein is stable for at least about: 30, 60, 90, 180, 360, 540, or 720 days, for example greater than 90 days, which can be measured by HPLC. In some embodiments, about: 80%, 85%, 90%, 95%, or 100% (e.g., about 95%) of the crystalline Form I of niraparib tosylate monohydrate is stable for 30 days or more.

In some embodiments, the pharmaceutical formulations described herein are stable with respect to compound degradation (e.g., less than 30%, degradation, less than 25% degradation, less than 20% degradation, less than 15% degradation, less than 10% degradation, less than 8% degradation, less than 5% degradation, less than 3% degradation, less than 2% degradation, or less than 5% degradation) over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, at least about 6 months, at least about 7 months, at least about 8 months, at least about 9 months, at least about 10 months, at least about 11 months, at least about 12 months, at least about 24 months, or at least about 36 months under storage conditions (e.g., room temperature). In some embodiments, the formulations described herein are stable with respect to compound degradation over a period of at least about 1 week. In some embodiments, the formulations described herein are stable with respect to compound degradation over a period of at least about 1 month. In some embodiments, the formulations described herein are stable with respect to compound degradation over a period of at least about 3 months. In some embodiments, the formulations described herein are stable with respect to compound degradation over a period of at least about 6 months. In some embodiments, the formulations described herein are stable with respect to compound degradation over a period of at least about 9 months. In some embodiments, the formulations described herein are stable with respect to compound degradation over a period of at least about 12 months.

Methods for assessing the chemical storage stability of solid dosage forms under accelerated aging conditions have been described in the literature. See, e.g., S. T. Colgan, T. J. Watson, R. D. Whipple, R. Nosal, J. V. Beaman, D. De Antonis, "The Application of Science and Risk Based Concepts to Drug Substance Stability Strategies" J. Pharm. Innov. 7:205-2013 (2012); Waterman K C, Carella A J, Gumkowski M J, et al Improved protocol and data analysis for accelerated shelf-life estimation of solid dosage forms. Pharm Res 2007; 24(4):780-90; and S. T. Colgan. R. J Timpano, D. Diaz, M. Roberts, R. Weaver, K. Ryan, K. Fields, G. Scrivens, Opportunities for Lean Stability Strategies" J. Pharm. Innov. 9:259-271 (2014).

Capsules

In some embodiments, the pharmaceutical composition is formulated into solid oral pharmaceutical dosage forms. Solid oral pharmaceutical dosage forms include, but are not limited to, tablets, capsules, powders, granules and sachets. For example, the solid oral pharmaceutical dosage form can be a capsule.

In some embodiments, a therapeutically effective amount of niraparib administered to a subject via a solid dosage form is in the range of about 1 mg to about 1000 mg. In some embodiments, the niraparib is niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1. In some embodiments, a therapeutically effective amount of niraparib administered to a subject via a solid dosage form is in the range of from about 50 mg to about 300 mg. In some embodiments, a therapeutically effective amount of niraparib administered to a subject via a solid dosage form is in the range of from about 50 mg to about 300 mg, wherein the niraparib is niraparib tosylate monohydrate is a crystalline Form I substantially free of Form II and Form III. Another embodiment provides the dosage form comprising niraparib as the crystalline Form I of niraparib tosylate monohydrate with an X-ray powder diffraction pattern substantially as shown in FIG. 1. In some embodiments, a niraparib formulation is administered as a solid dosage form at a concentration of about 50 mg to about 100 mg. In some embodiments, the niraparib formulation is administered as a solid dosage form at concentration of about 100 mg to about 300 mg. For example, a therapeutically effective amount of niraparib tosylate monohydrate crystalline Form I substantially free of Form II and Form III thereof administered to a subject via a solid dosage form can be from about 1 mg to 5 mg, 5 mg to 10 mg, 10 mg to 20 mg, 20 mg to 25 mg, 35 mg to 5 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg. For example, a therapeutically effective amount of niraparib tosylate monohydrate administered to a subject via a solid dosage form can be from about 1 mg to about 1000 mg, for example, from about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg. In some aspects, the solid oral dosage form can be administered one, two, or three times a day (b.i.d).

For example, a therapeutically effective amount of niraparib administered to a subject via a solid dosage form can be from about 1 mg to 5 mg, 5 mg to 10 mg, 10 mg to 20 mg, 20 mg to 25 mg, 25 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg. For example, a therapeutically effective amount of niraparib tosylate monohydrate administered to a subject via a solid dosage form can be from about 1 mg to 5 mg, 5 mg to 10 mg, 10 mg to 20 mg, 20 mg to 25 mg, 25 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg. In some embodiments, the niraparib is niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1. In some aspects, the solid oral dosage form can be administered one, two, or three times a day (b.i.d).

For example, a therapeutically effective amount of niraparib administered to a subject via a solid dosage form can be about 1 mg to 5 mg, 5 mg to 10 mg, 10 mg to 20 mg, 20 mg to 25 mg, 25 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg. For example, a therapeutically effective amount of niraparib tosylate monohydrate administered to a subject via a solid dosage form can be about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg. In some embodiments, the niraparib is niraparib tosylate monohydrate is a crystalline Form I substantially free of Form II and Form III. Another embodiment provides the composition wherein the crystalline Form I of niraparib tosylate monohydrate has an X-ray powder diffraction pattern substantially as shown in FIG. 1. In some embodiments, a therapeutically effective amount of niraparib tosylate monohydrate administered to a subject via a solid dosage form is about 79.7 mg. In some embodiments, a therapeutically effective amount of niraparib tosylate monohydrate administered to a subject via a solid dosage form is about 159.4 mg. In some embodiments, a therapeutically effective amount of niraparib tosylate monohydrate administered to a subject via a solid dosage form is about 159.4 mg, wherein the niraparib is niraparib tosylate monohydrate is a crystalline Form I substantially free of Form II and Form III In some embodiments, a therapeutically effective amount of niraparib tosylate monohydrate administered to a subject via a solid dosage form is about 318.8 mg. In some embodiments, a therapeutically effective amount of niraparib tosylate monohydrate administered to a subject via a solid dosage form is about 478.2 mg. In some aspects, the solid oral dosage form can be administered one, two, or three times a day (b.i.d).

Contemplated compositions of the present invention provide a therapeutically effective amount of niraparib over an interval of about 30 minutes to about 8 hours after administration, enabling, for example, once-a-day, twice-a-day, three times a day, and etc. administration if desired.

In some embodiments, the weight ratio of an active pharmaceutical ingredient (e.g., niraparib tosylate monohydrate is a crystalline Form I substantially free of Form II and Form III) to a non-active pharmaceutical ingredient (e.g., lactose monohydrate) is from about 1:10 to about 10:1, respectively, for example about 1:2, about 1:3, about 1:4, about 1:5, about 1:6, about 1:7, about 1:8, about 1:9, about 1:10, about 10-1, about 9:1, about 8:1, about 7:1, about 6:1, about 5:1, about 4-1, about 3-1, or about 2:1 In some embodiments, the weight ratio of an active pharmaceutical ingredient (e.g., niraparib tosylate monohydrate is a crystalline Form I substantially free of Form II and Form III) to a non-active pharmaceutical ingredient (e.g., magnesium stearate) is from about 10:1 to about 100:1, respectively, for example about 10:1, about 20.1, about 30:1, about 40:1, about 50:1, about 60:1, about 70:1, about 80:1, or about 90:1. In some embodiments, the weight ratio of a non-active pharmaceutical ingredient (e.g., lactose monohydrate or magnesium stearate) to an active pharmaceutical ingredient (e.g., niraparib tosylate monohydrate is a crystalline Form I substantially free of Form II and Form I) to is from about 3:2 to about 11:1, from about 3:1 to about 7:1, from about 1:1 to about 5:1, from about 9:2 to about 11:2, from about 4:2 to about 6:2, about 5:1, or about 2.5:1. In some embodiments, the weight ratio of an active pharmaceutical ingredient (e.g., niraparib tosylate monohydrate is a crystalline Form I substantially free of Form II and Form III) to a non-active pharmaceutical ingredient (e.g., lactose monohydrate or magnesium stearate) is about 1:1.6. In some embodiments, the weight ratio of an active pharmaceutical ingredient (e.g., niraparib tosylate monohydrate is a crystalline Form I substantially free of Form II and Form III) to a non-active pharmaceutical ingredient (e.g., lactose monohydrate or magnesium stearate) is about 1:2. In some embodiments, the weight ratio of niraparib tosylate monohydrate to lactose monohydrate is about 38:61, for example, 38.32:61.18. In some embodiments, the weight ratio of niraparib tosylate monohydrate to magnesium stearate is about 77:1, for example, 76.64:1.

In some embodiments, the weight ratio of a first non-active pharmaceutical ingredient to a second non-active pharmaceutical ingredient is from about 5:1 to about 200:1, respectively, for example about 5:1, about 10:1, about 20:1, about 40:1, about 50:1, about 75:1, about 100:1, about 110:1, about 120:1, about 130:1, about 140:1, about 150:1, about 160:1, about 170:1, about 180:1, about 190:1, or about 200:1 In some embodiments, the weight ratio of lactose monohydrate to magnesium stearate is about 120:1 to about 125:1. In some embodiments, the weight ratio of lactose monohydrate to magnesium stearate is about 122.36:1.

Indication Suitable for Treatment

Any subject having cancer, including breast cancer, ovarian cancer, cervical cancer, epithelial ovarian cancer, fallopian tube cancer, primary peritoneal cancer, endometrial cancer, prostate cancer, testicular cancer, pancreatic cancer, esophageal cancer, head and neck cancer, gastric cancer, bladder cancer, lung cancer (e.g., adenocarcinoma, NSCLC and SCLC), bone cancer (e.g., osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g., liposarcoma), bladder cancer, liver cancer (e.g., hepatocellular carcinoma), kidney cancer (e.g., renal cell carcinoma), myeloid disorders (e.g., AML, CML, myelodysplastic syndrome and promyelocytic leukemia), and lymphoid disorders (e.g., leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma) may be treated with compounds and methods described herein.

In some embodiments, the methods of the invention treat subjects with ovarian cancer. In some embodiments, the methods of the invention treat subjects with epithelial ovarian cancer. In some embodiments, the methods of the invention treat subjects with fallopian tube cancer. In some embodiments, the methods of the invention treat subjects with primary peritoneal cancer.

In some embodiments, the methods of the invention treat subjects with recurrent ovarian cancer. In some embodiments, the methods of the invention treat subjects with recurrent epithelial ovarian cancer. In some embodiments, the methods of the invention treat subjects with recurrent fallopian tube cancer. In some embodiments, the methods of the invention treat subjects with recurrent primary peritoneal cancer.

In some embodiments, the methods of the invention treat subjects with recurrent ovarian cancer following a complete or partial response to a chemotherapy, such as a platinum-based chemotherapy. In some embodiments, the methods of the invention treat subjects with recurrent epithelial ovarian cancer following a complete or partial response to a chemotherapy, such as a platinum-based chemotherapy. In some embodiments, the methods of the invention treat subjects with recurrent fallopian tube cancer following a complete or partial response to a chemotherapy, such as a platinum-based chemotherapy. In some embodiments, the methods of the invention treat subjects with recurrent primary peritoneal cancer following a complete or partial response to a chemotherapy, such as a platinum-based chemotherapy.

In some embodiments, the methods of the invention treat subjects with recurrent ovarian cancer, recurrent epithelial ovarian cancer, recurrent fallopian tube cancer and/or recurrent primary peritoneal cancer following a complete or partial response to a platinum-based chemotherapy, wherein the subjects begin the treatment no later than 8 weeks after their most recent platinum-containing regimen. For example, subjects can begin treatment with niraparib about 7 weeks after their most recent platinum-containing regimen. For example, subjects can begin treatment with niraparib about 6 weeks after their most recent platinum-containing regimen. For example, subjects can begin treatment with niraparib about 6 weeks after their most recent platinum-containing regimen. For example, subjects can begin treatment with niraparib about 5 weeks after their most recent platinum-containing regimen. For example, subjects can begin treatment with niraparib about 4 weeks after their most recent platinum-containing regimen. For example, subjects can begin treatment with niraparib about 3 weeks after their most recent platinum-containing regimen. For example, subjects can begin treatment with niraparib about 2 weeks after their most recent platinum-containing regimen. For example, subjects can begin treatment with niraparib about 1 week after their most recent platinum-containing regimen.

In some embodiments, the methods of the invention treat subjects with prostate cancer In some embodiments, the methods of the invention treat subjects with a pediatric cancer. Exemplary pediatric cancers include, but are not limited to adrenocortical carcinoma, astrocytoma, atypical teratoid rhabdoid tumor, brain tumors, chondroblastoma, choroid plexus tumor, craniopharyngioma, desmoid tumor, dysembryplastic neuroepithelial tumor (DNT), ependymoma, fibrosarcoma, germ cell tumor of the brain, glioblastoma multiforme, diffuse pontine glioma, low grade glioma, gliomatosis cerebri, hepatoblastoma, histiocytosis, kidney tumor, acute lymphoblastic leukemia (ALL), acute myeloid leukemia (AML), chronic myelogenous leukemia (CML), liposarcoma, liver cancer, Burkitt lymphoma, Hodgkin lymphoma, non-Hodgkin lymphoma, malignant fibrous histiocytoma, melanoma, myelodysplastic syndrome, nephroblastoma, neuroblastoma, neurofibrosarcoma, osteosarcoma, pilocytic astrocytoma, retinoblastoma, rhabdoid tumor of the kidney, rhabdomyosarcoma, Ewing sarcoma, soft tissue sarcoma, synovial sarcoma, spinal cord tumor and Wilm's tumor.

In some embodiments, the methods of the invention treat subjects with a cancer with a dosage of 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 300 mg, 850 mg, 900 mg, 950 mg, or 1000 mg of niraparib once-daily, twice-daily, or thrice-daily. In some embodiments, the methods of the invention treat subjects with a cancer with a dosage of 150 mg to 175 mg, 170 mg to 195 mg, 190 mg to 215 mg, 210 mg to 235 mg, 230 mg to 255 mg, 250 mg to 275 mg, 270 to 295 mg, 290 mg to 315 mg, 310 mg to 335 mg, 330 mg to 355 mg, 350 mg to 375 mg, or 370 mg to 400 mg of niraparib once-daily, twice-daily, or thrice-daily. In some embodiments, the methods of the invention treat subjects with a cancer with a dosage of 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg of niraparib once-daily, twice-daily, or thrice-daily.

In some embodiments, the methods of the invention treat subjects with a cancer with a dosage of from about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg of niraparib once-daily, twice-daily, or thrice-daily. In some embodiments, the methods of the invention treat subjects with a cancer with a dosage of from about 5 mg to 7.5 mg, 7 mg to 9.5 mg, 9 mg to 11.5 mg, 11 mg to 13.5 mg, 13 mg to 15.5 mg, 15 mg to 17.5 mg, 17 to 19.5 mg, 19 mg to 21.5 mg, 21 mg to 23/5 mg, 23 mg to 25.5 mg, 25 mg to 27.5 mg, 27 mg to 30 mg, 30 mg to 35 mg, 35 mg to 40 mg, 40 mg to 45 mg, 45 mg to 50 mg, 50 mg to 55 mg, 55 mg to 60 mg, 60 to 65 mg, 65 mg to 70 mg, 70 mg to 75 mg, 75 mg to 80 mg, 80 mg to 85 mg, 85 mg to 90 mg, 90 mg to 95 mg, or 95 mg to 100 mg of niraparib once-daily, twice-daily, or thrice-daily.

Administration of the Compositions

The recommended dose of the niraparib capsule formulations described herein as monotherapy is three 100 mg capsules taken orally once daily, equivalent to a total daily dose of 300 mg. Patients may be encouraged to take their dose at approximately the same time each day. Bedtime administration may be a potential method for managing nausea.

As described herein, doses of 1 to 1000 mg of niraparib may be administered for treatment of subjects, and methods and compositions described herein may comprise once-daily, twice-daily, or thrice-daily administration of a dose of up to 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, or 1000 mg once-daily, twice-daily, or thrice-daily. In some embodiments, the dose of niraparib is from 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 mg to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg, once-daily, twice-daily, or thrice-daily. In some embodiments, the methods of the invention treat subjects with a cancer with a dosage of 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, or 1000 mg of niraparib once-daily, twice-daily, or thrice-daily.

In some embodiments, a total daily dose of niraparib of 1 mg to 1000 mg, for example, or 50 to 300 mg, is administered. In some embodiments, the daily dose of niraparib is niraparib tosylate monohydrate is a crystalline Form I substantially free of Form II and Form III Another embodiment provides the daily dosage wherein the crystalline Form I of niraparib tosylate monohydrate has an X-ray powder diffraction pattern substantially as shown in FIG. 1. In some embodiments, the total daily dose of niraparib administered exceeds 100 mg per day. In some embodiments, the total daily dose of niraparib administered exceeds 200 mg per day. In some embodiments, the total daily dose of niraparib administered exceeds 300 mg per day. In some embodiments, the total daily dose of niraparib administered exceeds 400 mg per day. In some embodiments, the total daily dose of niraparib administered exceeds 500 mg per day.

In some embodiments, the total daily dose of niraparib administered does not exceed 500 mg per day. In some embodiments, the daily dose of niraparib is niraparib tosylate monohydrate is a crystalline Form I substantially free of Form II and Form III. Another embodiment provides the daily dosage wherein the crystalline Form I of niraparib tosylate monohydrate has an X-ray powder diffraction pattern substantially as shown in FIG. 1. In some embodiments, the total daily dose of niraparib administered does not exceed 300 mg per day. In some embodiments, the total daily dose of niraparib administered does not exceed 100 mg per day. In some embodiments, the total daily dose of niraparib administered does not exceed 50 mg per day. In some embodiments, the total daily dose of niraparib is from about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg, the total daily dose of niraparib is about 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, or 1000 mg. In some embodiments, the daily dose of niraparib is niraparib tosylate monohydrate is a crystalline Form I substantially free of Form II and Form III. Another embodiment provides the daily dosage wherein the crystalline Form I of niraparib tosylate monohydrate has an X-ray powder diffraction pattern substantially as shown in FIG. 1.

A therapeutically effective dose of niraparib tosylate monohydrate as a crystalline Form I substantially free of Form II and Form III is about 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, or 1000 mg per day. In some embodiments, the amount of niraparib administered daily is from about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg per day.

In some embodiments, the amount of niraparib tosylate monohydrate as a crystalline Form I substantially free of Form II and Form III is administered one time daily is 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg. In some embodiments, the amount of niraparib administered one time daily is 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, or 1000 mg.

In some embodiments, the amount of niraparib tosylate monohydrate as a crystalline Form I substantially free of Form II and Form III is administered two times daily is 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg. In some embodiments, the amount of niraparib administered two times daily is 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, or 1000 mg.

In some embodiments, the amount of niraparib tosylate monohydrate as a crystalline Form I substantially free of Form II and Form III is administered three times daily is 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg. In some embodiments, the amount of niraparib administered three times daily is 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, or 1000 mg.

In some embodiments, the niraparib tosylate monohydrate as a crystalline Form I substantially free of Form II and Form III is present at a dose from about 1 mg to about 1000 mg, including, but not limited to, about 1 mg, 5 mg, 10.0 mg, 10.5 mg, 11.0 mg, 11.5 mg, 12.0 mg, 12.5 mg, 13.0 mg, 13.5 mg, 14.0 mg, 14.5 mg, 15.0 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 34 mg, 34.5 mg, 35 mg, 35.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 120.5 mg, 121 mg, 121.5 mg, 122 mg, 122.5 mg, 123 mg, 123.5 mg, 124 mg, 124.5 mg, 125 mg, 125.5 mg, 126 mg, 126.5 mg, 127 mg, 127.5 mg, 128 mg, 128.5 mg, 129 mg, 129.5 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, or 1000 mg.

In some embodiments, the niraparib tosylate monohydrate as a crystalline Form I substantially free of Form II and Form III is present at a dose from about 1 mg to 5 mg, 5 mg to 10 mg, 10 mg to 20 mg, 20 mg to 25 mg, 25 mg to 100 mg, 35 mg to 140 mg, 70 mg to 140 mg, 80 mg to 135 mg, 10 mg to 25 mg, 25 mg to 50 mg, 50 mg to 100 mg, 100 mg to 150 mg, 150 mg to 200 mg, 10 mg to 35 mg, 35 mg to 70 mg, 70 mg to 105 mg, 105 mg to 140 mg, 140 mg to 175 mg, or 175 mg to 200 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg.

Frequency of Administration

In some embodiments, a composition disclosed herein is administered to an individual in need thereof once. In some embodiments, a composition disclosed herein is administered to an individual in need thereof more than once. In some embodiments, a first administration of a composition disclosed herein is followed by a second administration of a composition disclosed herein. In some embodiments, a first administration of a composition disclosed herein is followed by a second and third administration of a composition disclosed herein. In some embodiments, a first administration of a composition disclosed herein is followed by a second, third, and fourth administration of a composition disclosed herein. In some embodiments, a first administration of a composition disclosed herein is followed by a second, third, fourth, and fifth administration of a composition disclosed herein. In some embodiments, a first administration of a composition disclosed herein is followed by a drug holiday.

The number of times a composition is administered to an individual in need thereof depends on the discretion of a medical professional, the disorder, the severity of the disorder, and the individual's response to the formulation. In some embodiments, a composition disclosed herein is administered once to an individual in need thereof with a mild acute condition. In some embodiments, a composition disclosed herein is administered more than once to an individual in need thereof with a moderate or severe acute condition. In the case wherein the patient's condition does not improve, upon the doctor's discretion the administration of niraparib may be administered chronically, that is, for an extended period of time, including throughout the duration of the patient's life in order to ameliorate or otherwise control or limit the symptoms of the patient's disease or condition.

In some embodiments, the niraparib composition is administered at predetermined time intervals over an extended period of time. In some embodiments, the niraparib composition is administered once every day. In some embodiments, the niraparib composition is administered every other day. In some embodiments, the niraparib composition is administered over 1 week, 2 weeks, 1 month, 2 months, 3 months, 6 moths, 1 year, 2 years, 3 years, 4 years, 5 years, 6 years, 7 years, 8 years, 9 years, 10 years, 11 years, or 12-15 years.

In some embodiments, the niraparib composition is administered in doses having a dose-to-dose niraparib concentration variation of less than 50%, less than 40%, less than 30%, less than 20%, less than 10%, or less than 5%.

In the case wherein the patient's status does improve, upon the doctor's discretion the administration of the niraparib may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. A first or second dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. For example, a first or second dose reduction during a drug holiday may be a dose reduced from 5 mg to 1 mg, 10 mg to 5 mg, 20 mg to 10 mg, 25 mg to 10 mg, 50 mg to 25 mg, 75 mg to 50 mg, 75 mg to 25 mg, 100 mg to 50 mg, 150 mg to 75 mg, 100 mg to 25 mg, 200 mg to 100 mg, 200 to 50 mg, 250 mg to 100 mg, 300 mg to 50 mg, 300 mg to 100 mg, 300 mg to 200 mg, 400 mg to 50 mg, 400 mg to 100 mg, 400 mg to 200 mg, 500 mg to 50 mg, 500 mg to 100 mg, 500 mg to 250 mg, 1000 mg to 50 mg, 1000 mg to 100 mg, or 1000 mg to 500 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, or 950 mg to 1000 mg. For example, a first or second dose reduction during a drug holiday may be a dose reduced by 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, or 1000 mg.

Once improvement of the patient's condition has occurred, a maintenance niraparib dose is administered if necessary. Subsequently, the dosage or the frequency of administration, or both, is optionally reduced, as a function of the symptoms, to a level at which the improved disease, disorder or condition is retained. In certain embodiments, patients require intermittent treatment on a long-term basis upon any recurrence of symptoms.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed with invention as defined in the claims which follow. The invention disclosed herein is further illustrated by the following examples which in no way should be construed as being limiting.

Experimental Techniques

X-ray Powder Diffraction (XRPD)

The Rigaku Smart-Lab X-ray diffraction system was configured for reflection Bragg-Brentano geometry using a line source X-ray beam. The x-ray source is a Cu Long Fine Focus tube that was operated at 40 kV and 44 ma. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2 θ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. Each sample was analyzed from 2 to 40° 2θ using a continuous scan of 6° 2θ per minute with an effective step size of 0.02° 2θ. Unless otherwise noted, XPRD studies were performed at room temperature and room humidity.

Differential Scanning Calorimetry (DSC)

DSC analyses were carried out using a TA Instruments Q2000 instrument The instrument temperature calibration was performed using indium. The DSC cell was kept under a nitrogen purge of ~50 mL per minute during each analysis. The sample was placed in a standard, crimped, aluminum pan and was heated from 25° C. to 350° C. at a rate of 10° C. per minute.

Dynamic Vapor Sorption (DVS) Analysis

DVS analyses were carried out TA Instruments Q5000 Dynamic Vapor Sorption analyzer. The instrument was calibrated with standard weights and a sodium bromide standard for humidity. Samples were analyzed at 25° C. with a maximum equilibration time of 60 minutes in 10% relative humidity (RH) steps from 5 to 95% RH (adsorption cycle) and from 95 to 5% RH (desorption cycle).

Example 1: Water Activity Studies

Slurry experiments designed to provide a range of water activities were carried out in solvent mixtures containing water and dimethylsulfoxide (Table 1). The anhydrate appears to be the preferred form at water activities of 0.11 or less and the monohydrate appears to be the preferred form at water activities of 0.22 or more. The amorphous halo observed in many of the patterns is due to solvent. The samples were analyzed while wet to avoid changes, such as the hydrate converting to the anhydrate, from drying.

TABLE 1

| Solvent (% water in DMSO) | Water activity | Time (days) | XRPD Result |
| --- | --- | --- | --- |
| 0 | 0 | 2 | anhydrate |
| 9.8 | 0.11 | 2 | anhydrate |
| 17.2 | 0.22 | 2 | hydrate |
| 27.6 | 0.38 | 2 | hydrate |
| 43.3 | 0.60 | 2 | hydrate |
| 82.8 | 0.84 | 2 | hydrate |
| 100.0 | 1.00 | 2 | hydrate |

Figure 6:
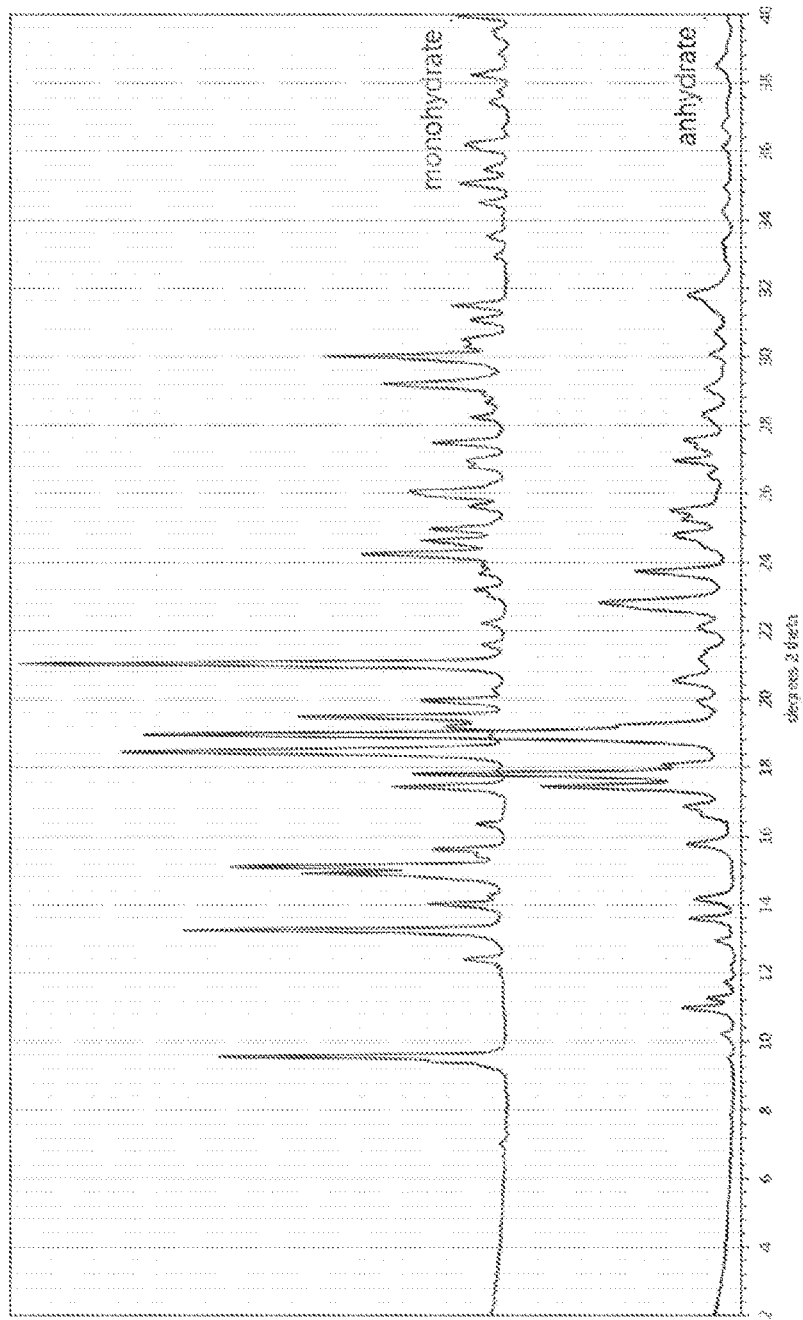
FIG. 6 shows an overlay of exemplary X-ray powder diffraction patterns for crystalline Form I, and Form III of 2-{4-[(3S)-piperidin-3-yl]phenyl}-2H-indazole-7-carboxamide.

Example 2: Preparation of Form I of 2-{4-[(3S)-piperidin-3-yl]phenyl}-2H-indazole-7-carboxamide A batch of 2-{4-[(3S)-piperidin-3-yl]phenyl}-2H-indazole-7-carboxamide tosylate which is a mixture of Form I, Form II and Form II is dissolved in water:DMSO/200:1 to reach a concentration of about 0.15 M. The resulting mixture is heated until dissolution occurs and is then cooled to about 25° C. overnight. The resulting solid is collected, dried and analyzed by x-ray powder diffraction, differential scanning calorimetry, Raman spectroscopy, infrared spectroscopy, dynamic water vapor sorption, or any combination thereof, to determine the presence of Form II or Form III. FIG. 6 provides an overlay comparison of the x-ray powder diffraction patterns for Form I and Form III. FIG. 9 provides an overlay comparison of the x-ray powder diffraction patterns for Form I, Form II and Form III.

Example 3: Preparation of Anhydrous Form III of 2-{4-[(3S)-piperidin-3-yl]phenyl}-2H-indazole-7-carboxamide Niraparib 4-toluenesulfonate monohydrate (3.01 g) was suspended in 110 mL of toluene, and the resulting mixture was heated to reflux for 2 hours, collecting toluene/water into a Dean-Stark trap. A small amount of water was observed in the trap. The slurry was allowed to cool to ambient temperature, vacuum filtered, and the solids air dried.

Example 4: Characterization of Form I of 2-{4-[(3S)-piperidin-3-yl]phenyl}-2H-indazole-7-carboxamide X-Ray Powder Diffraction
FIGS. 1 and 6 provide the X-ray powder diffraction pattern for crystalline Form I monohydrate of 2-{4-[(3S)-piperidin-3-yl]phenyl}-2H-indazole-7-carboxamide. Table 2 provides a listing of the reflections.

TABLE 2

| Pos. [°2Th.] | d-spacing [Å] | Height [cts] | FWHM [°2Th.] |
|---|---|---|---|
| 6.5879 | 13.40619 | 460.5 | 0.5288 |
| 6.985 | 12.64485 | 477.57 | 0.823 |
| 9.0602 | 9.75275 | 2868.98 | 0.4263 |
| 9.524 | 9.27879 | 78535.62 | 0.1109 |
| 11.7927 | 7.49835 | 1707.43 | 0.1.243 |
| 12.355 | 7.15828 | 54936.48 | 0.1168 |
| 12.6092 | 7.01457 | 1188.76 | 0.0993 |
| 13.2213 | 6.69113 | 35563.92 | 0.1254 |
| 13.5062 | 6.55063 | 569.25 | 0.3698 |
| 13.8394 | 6.39368 | 6772.92 | 0.1125 |
| 13.9958 | 6.32258 | 6011.08 | 0.1324 |
| 14.1943 | 6.23457 | 16335.01 | 0.1248 |
| 14.6912 | 6.0248 | 24730.51 | 0.1255 |
| 14.858 | 5.95753 | 27991.59 | 0.1169 |
| 15.0707 | 5.87396 | 18385.48 | 0.1353 |
| 15.3794 | 5.75672 | 2780.53 | 0.1073 |
| 15.5881 | 5.68013 | 3779.759 | 0.1025 |
| 16.3332 | 5.42265 | 9823.46 | 0.1415 |
| 16.617 | 5.33067 | 2329.47 | 0.201 |
| 17.4264 | 5.08485 | 50122.63 | 0.1333 |
| 17.573 | 5.042.76 | 8100.61 | 0.3643 |
| 17.8849 | 4.95552 | 2229.24 | 0.1546 |
| 18.427 | 4.81093 | 204163.1 | 0.1721 |
| 18.8482 | 4.70436 | 3012.17 | 0.1544 |
| 19.177 | 4.62444 | 14586.06 | 0.166 |
| 19.4706 | 4.55535 | 8731.12 | 0.1299 |
| 19.9266 | 4.45213 | 21822.89 | 0.1538 |
| 20.2412 | 4.38364 | 6045.22 | 0.1614 |
| 21.0044 | 4.22605 | 63640.16 | 0.1445 |
| 21.5548 | 4.11937 | 10560.25 | 0.1515 |
| 22.2131 | 3.99876 | 753.36 | 0.1605 |
| 22.9905 | 3.8652.6 | 4058.7 | 0.1646 |
| 23.1768 | 3.83462 | 7387.16 | 0.1302 |
| 23.6115 | 3.76499 | 6636.48 | 0.3093 |

TABLE 2-continued

| Pos. [°2Th.] | d-spacing [Å] | Height [cts] | FWHM [°2Th.] |
|---|---|---|---|
| 23.8073 | 3.73447 | 3271.55 | 0.0929 |
| 24.2164 | 3.6723 | 21759.7 | 0.1697 |
| 24.4265 | 3.64119 | 6345.06 | 0.161 |
| 24.9128 | 3.5712 | 103096 | 0.1575 |
| 25.5764 | 3.48002 | 47498.83 | 0.1529 |
| 26.0348 | 3.41979 | 99687.98 | 0.1845 |
| 26.9234 | 3.3089 | 32700.42 | 0.1866 |
| 27.4696 | 3.24434 | 21472.77 | 0.1595 |
| 27.9243 | 3.19253 | 1792.33 | 0.1146 |
| 28.3295 | 3.14778 | 1967.85 | 0.8105 |
| 28.6335 | 3.11505 | 13930.93 | 0.1549 |
| 29.1807 | 3.05787 | 12702.19 | 0.1798 |
| 29.6703 | 3.00852 | 6677.41 | 0.4434 |
| 29.9963 | 2.97655 | 16868.65 | 0.1759 |
| 30.3008 | 2.94733 | 6812.67 | 0.1494 |
| 30.508 | 2.92779 | 14421.1 | 0.1956 |
| 31.0316 | 2.87957 | 5755.4 | 0.1828 |
| 31.5213 | 2.83594 | 5497.13 | 0.179 |
| 32.575 | 2.74657 | 498.46 | 0.1586 |
| 32.9187 | 2.71867 | 3851.61 | 0.2345 |
| 33.532 | 2.67034 | 2240.41 | 0.2865 |
| 33.8569 | 2.64546 | 1516.95 | 0.2802 |
| 34.4808 | 2.599 | 1196.67 | 0.1616 |
| 35.0202 | 2.5602 | 3988.39 | 0.2523 |
| 35.4178 | 2.53236 | 2443.9 | 0.1374 |
| 35.5372 | 2.52412 | 2795 | 0.2115 |
| 36.1608 | 2.48202 | 5523.84 | 0.2396 |
| 37.3996 | 2.4026 | 5344.49 | 0.2021 |
| 37.7359 | 2.38196 | 1623.87 | 0.2622 |
| 38.2141 | 2.35324 | 4115.75 | 0.203 |
| 38.55 | 2.33351 | 1414.01 | 0.1982 |
| 38.8559 | 2.31584 | 6323.46 | 0.1835 |
| 30.508 | 2.92779 | 14421.1 | 0.1956 |
| 31.0316 | 2.87957 | 5755.4 | 0.1828 |

Differential Scanning Calorimetry (DSC)
FIG. 2 shows an exemplary scanning differential calorimetry pattern for crystalline monohydrate Form I of 2-{4-[(3S)-piperidin-3-yl]phenyl}-2H-indazole-7-carboxamide. The DSC curve of the monohydrate exhibits an endotherm at approximately 154° C. which is likely due to dehydration followed by an endotherm at approximately 231° C. which is likely due to melting.

Dynamic Vapor Sorption (DVS) Analysis
FIG. 5 shows an exemplary dynamic water vapor sorption pattern for crystalline Form I of 2-{4-[(3S)-piperidin-3-yl]phenyl}-2H-indazole-7-carboxamide. The DVS curve of the monohydrate indicates the monohydrate is not hygroscopic. After the experiment the samples were analyzed by XRPD. The monohydrate remained unchanged.

Example 5: Characterization of anhydrous Form III of 2-{4-[(3S)-piperidin-3-yl]phenyl}-2H-indazole-7-carboxamide X-Ray Powder Diffraction
FIGS. 6 and 7 provide the X-ray powder diffraction pattern for crystalline anhydrous Form III of 2-{4-[(3S)-piperidin-3-yl]phenyl}-2H-indazole-7-carboxamide. Table 3 provides a listing of the reflections.

TABLE 3

| Pos. [°2Th.] | d-spacing [Å] | Height [cts] | FWHM [°2Th.] |
|---|---|---|---|
| 7.8499 | 11.25339 | 895.67 | 0.1707 |
| 9.5009 | 9.3012.6 | 2320.94 | 0.1654 |
| 10.2259 | 8.64344 | 4750.18 | 0.2032 |
| 10.9698 | 8.05886 | 18992.07 | 0.164 |
| 11.2525 | 7.85708 | 10175.98 | 0.1595 |

TABLE 3-continued

| Pos. [°2Th.] | d-spacing [Å] | Height [cts] | FWHM [°2Th.] |
|---|---|---|---|
| 11.7171 | 7.54655 | 3014.31 | 0.1668 |
| 12.1661 | 7.26901 | 1145.84 | 0.2273 |
| 12.9299 | 6.84128 | 6553.68 | 0.1857 |
| 13.5713 | 6.51937 | 14717.58 | 0.1828 |
| 14.1376 | 6.25944 | 13082.42 | 0.2387 |
| 15.78 | 5.61146 | 13659.23 | 0.236 |
| 16.6445 | 5.3219 | 10574.32 | 0.39 |
| 16.8657 | 5.25261 | 9058.46 | 0.3716 |
| 17.4485 | 5.07847 | 51335.75 | 0.2087 |
| 17.814 | 4.97508 | 86267.17 | 0.1798 |
| 18.0524 | 4.90991 | 19854.59 | 0.2729 |
| 18.9679 | 4.67494 | 123782.4 | 0.199 |
| 19.1913 | 4.62102 | 31339.04 | 0.4525 |
| 19.9466 | 4.44771 | 3909.81 | 0.1923 |
| 20.5575 | 4.3169 | 10356.35 | 0.2796 |
| 21.2948 | 4.16907 | 3968.5 | 0.4668 |
| 22.0804 | 4.02248 | 4071.42 | 0.1664 |
| 22.7882 | 3.89912 | 32060.48 | 0.3358 |
| 23.7401 | 3.74489 | 21269.23 | 0.2247 |
| 24.8296 | 3.58298 | 11374.86 | 0.3818 |
| 25.2491 | 3.5244 | 9542.6 | 0.2188 |
| 25.471 | 3.49419 | 12822.77 | 0.2109 |
| 25.9789 | 3.42702 | 898.11 | 0.3533 |
| 26.5278 | 3.35734 | 1135.46 | 0.3302 |
| 26.9336 | 3.30767 | 8691.48 | 0.176 |
| 27.3191 | 3.26186 | 4697.95 | 0.304 |
| 27.5324 | 3.23707 | 7412.05 | 0.279 |
| 28.3515 | 3.14539 | 5097.68 | 0.1787 |
| 29.1345 | 3.06262 | 4974.1 | 0.254 |
| 29.6226 | 3.01325 | 685.05 | 0.0579 |
| 30.06 | 2.97039 | 3581.07 | 0.1928 |
| 30.6913 | 2.91071 | 1865.07 | 0.223 |
| 31.7871 | 2.81283 | 8828.05 | 0.5478 |
| 32.9385 | 2.71709 | 884.34 | 0.3145 |
| 33.3656 | 2.68328 | 1576.57 | 0.2445 |
| 34.2199 | 2.61822 | 1560.9 | 0.3393 |
| 34.9489 | 2.56526 | 699.93 | 0.2234 |
| 36.0738 | 2.4878 | 1800.14 | 0.2491 |
| 36.7177 | 2.44564 | 2321.23 | 0.3452 |
| 37.1849 | 2.41597 | 800.76 | 0.3354 |
| 38.4831 | 2.33741 | 2823.91 | 0.3912 |
| 38.7512 | 2.32185 | 925.86 | 0.3342 |
| 39.0789 | 2.30313 | 877.67 | 0.3596 |
| 39.8123 | 2.26238 | 765.08 | 0.5313 |

Differential Scanning Calorimetry (DSC)

FIG. 2 shows an exemplary scanning differential calorimetry pattern for crystalline anhydrous Form III of 2-{4-[(3S)-piperidin-3-yl]phenyl}-2H-indazole-7-carboxamide. The DSC curve of the anhydrate exhibits an endotherm at approximately 230° C. which is likely due to melting.

Dynamic Vapor Sorption (DVS) Analysis

FIG. 8 shows an exemplary dynamic water vapor sorption pattern for crystalline anhydrous Form III of 2-{4-[(3S)-piperidin-3-yl]phenyl}-2H-indazole-7-carboxamide. The DVS curve of the anhydrate is very hygroscopic and showed a weight gain of approximately 15.8% up to 95% RH. After the experiment the samples were analyzed by XRPD. The anhydrate converted to the monohydrate.

Paragraphs of the Embodiments

A composition comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide.

The composition of paragraph [00133], wherein the crystalline Form I of 2-{4-[(3S)-piperidin-3-yl]phenyl}-2H-indazole-7-carboxamide has an X-ray powder diffraction pattern substantially as shown in FIG. 1.

The composition of paragraph [00133] or [00134], wherein the crystalline Form I of 2-{4-[(3S)-piperidin-3-yl]phenyl}-2H-indazole-7-carboxamide is characterized by at least one X-ray diffraction pattern reflection selected from a 2θ value of 9.5±0.2, 12.4±0.2, 13.2±0.2, 17.4±0.2, 18.4±0.2, 21.0±0.2, 24 9±0.2, 25.6±0.2, 26.0±0.2, and 26.9±0 2.

The composition of any one of paragraphs [00133]-[00135], wherein the crystalline Form I of 2-{4-[(3S)-piperidin-3-yl]phenyl}-2H-indazole-7-carboxamide is characterized by an X-ray diffraction pattern reflection at 2θ=24.9±0.2.

The composition of paragraph [00136], wherein the crystalline Form I is further characterized by X-ray diffraction pattern reflections at 2θ value of 9.5±0.2 and 26.0±0.2.

The composition of paragraph [00136] or [00137], wherein the crystalline Form I is further characterized by X-ray diffraction pattern reflections at a 2θ value of 12.4±0.2, 13.2±0.2, 17.4±0.2, 18.4±0.2, 21.0±0.2, 25.6±0.2, and 26.9±0.2.

The composition of paragraph [00136] or [00137], wherein the crystalline Form I is further characterized by at least one X-ray diffraction pattern reflection selected from a 2θ value of 12.4±0.2, 13.2±0.2, 17.4±0.2, 18.4±0.2, 21.0±0.2, 25.6±0.2, and 26.9±0.2.

The composition of paragraph [00136] or [00137], wherein the crystalline Form I is further characterized by at least two X-ray diffraction pattern reflections selected from a 2θ value of 12.4±0.2, 13.2±0.2, 17.4±0.2, 18.4±0.2, 21.0±0.2, 25.6±0.2, and 26.9±0.2.

The composition of paragraph [00136] or [00137], wherein the crystalline Form I is further characterized by at least three X-ray diffraction pattern reflections selected from a 2θ value of 12.4±0.2, 13.2±0.2, 17.4±0.2, 18.4±0.2, 21.0±0.2, 25.6±0.2, and 26.9±0.2.

The composition of paragraph [00136] or [00137], wherein the crystalline Form I is further characterized by at least four X-ray diffraction pattern reflections selected from a 2θ value of 12.4±0.2, 13.2±0.2, 17 4±0.2, 18.4±0.2, 21.0±0.2, 25.6±0 2, and 26.9±0.2.

A composition comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide, wherein the crystalline Form I is characterized by a scanning differential calorimetry pattern substantially as shown in FIG. 2.

The composition of paragraph [00143], wherein the composition is the composition of any one of paragraphs [00133]-[00142].

A composition comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide, wherein the crystalline Form I is characterized by a Raman spectroscopy pattern substantially as shown in FIG. 3.

The composition of paragraph [00145], wherein the composition is the composition of any one of paragraphs [00133]-[00144].

A composition comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide, wherein the crystalline Form I is characterized by a dynamic water vapor sorption pattern substantially as shown in FIG. 5.

The composition of paragraph [00147], wherein the composition is the composition of any one of paragraphs [00133]-[00146].

A composition comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide, wherein the crystalline Form I is characterized by an infrared spectroscopy pattern substantially as shown in FIG. 4.

The composition of paragraph [00149], wherein the composition is the composition of any one of paragraphs [00133]-[00148].

The composition of any one of paragraphs [00133]-[00150], wherein the presence of Form III is characterized by at least one X-ray diffraction pattern reflection selected from a 2θ value of 17.8±0.2, 19.0±0.2, or 22.8±0.2.

The composition of any one of paragraphs [00133]-[00151], wherein substantially free of Form II and Form III means less than about 20% (w/w) combined total weight for Form II and Form III compared to the combined total weight of Form I. Form II and Form III.

The composition of any one of paragraphs [00133]-[00151], wherein substantially free of Form II and Form III means less than about 15% (w/w) combined total weight for Form II and Form III compared to the combined total weight of Form I, Form II and Form III.

The composition of any one of paragraphs [00133]-[00151], wherein substantially free of Form II and Form III means less than about 10% (w/w) combined total weight for Form II and Form III compared to the combined total weight of Form I, Form II and Form III.

The composition of any one of paragraphs [00133]-[00151], wherein substantially free of Form II and Form II means less than about 8% (w/w) combined total weight for Form II and Form III compared to the combined total weight of Form I, Form II and Form III.

The composition of any one of paragraphs [00133]-[00151], wherein substantially free of Form II and Form III means less than about 6% (w/w) combined total weight for Form II and Form III compared to the combined total weight of Form I. Form II and Form III.

The composition of any one of paragraphs [00133]-[00151], wherein substantially free of Form II and Form III means less than about 4% (w/w) combined total weight for Form II and Form III compared to the combined total weight of Form I, Form II and Form II.

The composition of any one of paragraphs [00133]-[00151], wherein substantially free of Form I and Form III means less than about 3% (w/w) combined total weight for Form II and Form III compared to the combined total weight of Form I. Form II and Form III.

The composition of any one of paragraphs [00133]-[00151], wherein substantially free of Form II and Form II means less than about 2% (w/w) combined total weight for Form II and Form III compared to the combined total weight of Form I, Form II and Form III.

The composition of any one of paragraphs [00133]-[00151], wherein substantially free of Form II and Form II means less than about 1% (w/w) combined total weight for Form II and Form III compared to the combined total weight of Form I, Form II and Form III.

A composition comprising crystalline Form II of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide and crystalline Form III of 2-{4-[(3S)-piperidin-3-yl]phenyl}-2H-indazole-7-carboxamide.

A composition comprising crystalline Form II of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide.

A composition comprising crystalline Form II 2-{4-[(3S)-piperidin-3-yl]phenyl}-2H-indazole-7-carboxamide and crystalline Form III of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide.

The composition of any one of paragraphs [00161]-[00163], wherein the crystalline Form II is characterized by at least one X-ray diffraction pattern reflection selected from a 2θ value of 9.7±0.3, 12.8±0.3, 17.9±0.3, 19.7±0.3, and 21.8±0.3.

The composition of any one of paragraphs [00161]-[00164], wherein the crystalline Form II has an X-ray powder diffraction pattern substantially as shown in FIG. 9 for Form II.

A composition comprising crystalline Form III of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide and crystalline Form II of 2-{4-[(3S)-piperidin-3-yl]phenyl}-2H-indazole-7-carboxamide.

A composition comprising crystalline Form III of 2-{4-[(3S)-piperidin-3-yl]phenyl}-2H-indazole-7-carboxamide substantially free of crystalline Form I of 2-{4-[(3S)-piperidin-3-yl]phenyl}-2H-indazole-7-carboxamide.

The composition of any one of paragraphs [00163]-[00167], wherein the crystalline Form III is characterized by at least one X-ray diffraction pattern reflection selected from a 2θ value of 17.8±0.2, 19.0±0.2, or 22.8±0.2.

The composition of any one of paragraphs [00163]-[00167] wherein the crystalline Form III has an X-ray powder diffraction pattern substantially as shown in FIG. 9 for Form III.

The composition of any one of paragraphs [00163]-[00167], wherein the crystalline Form III of 2-{4-[(3S)-piperidin-3-yl]phenyl}-2H-indazole-7-carboxamide has an X-ray powder diffraction pattern substantially as shown in FIG. 7.

The composition of any one of paragraphs [00163]-[00170], wherein the crystalline Form III of 2-{4-[(3S)-piperidin-3-yl]phenyl}-2H-indazole-7-carboxamide characterized by a dynamic water vapor sorption pattern substantially as shown in FIG. 8.

The composition of any one of paragraphs [00163]-[00171], wherein the crystalline Form III of 2-{4-[(3S)-piperidin-3-yl]phenyl}-2H-indazole-7-carboxamide characterized by a scanning differential calorimetry pattern substantially as shown in FIG. 2.

A method of making crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide, comprising dissolving a composition comprising Form II of 2-{4-[(3S)-piperidin-3-yl]phenyl}-2H-indazole-7-carboxamide or Form III of 2-{4-[(3S)-piperidin-3-yl]phenyl}-2H-indazole-7-carboxamide, or a mixture thereof, in a solvent having a water:organic solvent ratio of about 10:1 to about 400:1 (v/v), and crystallizing the crystalline Form I.

The method of paragraph [00173], wherein the water:organic solvent ratio is about 10:1 (v/v), about 50:1 (v/v), about 100:1 (v/v), about 200:1 (v/v), about 300:1 (v/v), or about 400:1 (v/v).

The method of paragraph [00173], wherein the organic solvent is a polar solvent, a polar protic solvent, a polar aprotic solvent, an ether-containing solvent, or any combination thereof.

The method of paragraph [00173], wherein the organic solvent is 2-propanol, acetone, methyl ethyl ketone, acetonitrile, acetic acid, formic acid, methyl tert-butyl ether, dioxane, dimethyl sulfoxide, or any combination thereof.

The method of paragraph [00173], wherein the organic solvent is acetone, methyl ethyl ketone, acetonitrile, methyl tert-butyl ether, dioxane, dimethyl sulfoxide, or any combination thereof.

The method of paragraph [00173], wherein the organic solvent is 2-propanol, acetic acid, formic acid, or any combination thereof.

The method of paragraph [00173], wherein the organic solvent and water is heated prior to crystallization.

A composition comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide as described in any one of paragraphs 1-[00160], prepared by dissolving a composition comprising Form II of 2-{4-[(3S)-piperidin-3-yl]phenyl}-2H-indazole-7-carboxamide or Form III of 2-{4-[(3S)-piperidin-3-yl]phenyl}-2H-indazole-7-carboxamide, or a mixture thereof, in a solvent having a water:organic solvent ratio of about 10:1 to about 400:1 (v/v), and crystallizing the crystalline Form I.

The composition of paragraph [00180], wherein the water:organic solvent ratio is about 10:1 (v/v), about 50:1 (v/v), about 100:1 (v/v), about 200:1 (v/v), about 300:1 (v/v), or about 400:1 (v/v).

The composition of paragraph [00180], wherein the organic solvent is a polar solvent, a polar protic solvent, a polar aprotic solvent, an ether-containing solvent, or any combination thereof.

The composition of paragraph [00180], wherein the organic solvent is 2-propanol, acetone, methyl ethyl ketone, acetonitrile, acetic acid, formic acid, methyl tert-butyl ether, dioxane, dimethyl sulfoxide, or any combination thereof.

The composition of paragraph [00180], wherein the organic solvent is acetone, methyl ethyl ketone, acetonitrile, methyl tert-butyl ether, dioxane, dimethyl sulfoxide, or any combination thereof.

The composition of paragraph [00180], wherein the organic solvent is 2-propanol, acetic acid, formic acid, or any combination thereof.

The composition of paragraph [00180], wherein the organic solvent and water is heated prior to crystallization.

The composition of any one of paragraphs [00133]-[00172] and [00180]-[00186], wherein the composition is a pharmaceutical composition.

A pharmaceutical composition comprising crystalline Form I of 2-{4-[(3S)-piperidin-3-yl]phenyl}-2H-indazole-7-carboxamide substantially free of Form II and Form III of 2-{4-[(3S)-piperidin-3-yl]phenyl}-2H-indazole-7-carboxamide, and at least one pharmaceutically acceptable excipient.

The pharmaceutical composition of any one of paragraphs [00133]-[00188], wherein the composition is in an oral dosage form.

The pharmaceutical composition of paragraph [00189], wherein the oral dosage form is a tablet or capsule.

An article of manufacture comprising multiple unit doses of the pharmaceutical composition of any of paragraphs [00187]-[00190] in a sealed container with written instructions for use.

The article of manufacture of paragraph [00191], further comprising an induction seal, desiccant, or any combination thereof.

The pharmaceutical composition of paragraph [00187] or [00188] wherein the composition is in unit dose form.

What is claimed is:

1. A crystalline Form I of 2-{4-[(3S)-piperidin-3-yl]phenyl}-2H-indazole-7-carboxamide tosylate monohydrate substantially free of Form II of 2-{4-[(3S)-piperidin-3-yl]phenyl}-2H-indazole-7-carboxamide tosylate, non-stoichiometric hydrate and Form III of 2-{4-[(3S)-piperidin-3-yl]phenyl}-2H-indazole-7-carboxamide tosylate anhydrate, wherein the crystalline Form I of 2-{4-[(3S)-piperidin-3-yl]phenyl}-2H-indazole-7-carboxamide tosylate monohydrate is characterized by an X-ray powder diffraction (XRPD) pattern comprising diffraction angles at 2θ values of 9.5±0.2, 24.9±0.2, and 26.0±0.2 degrees; and wherein substantially free of Form II and Form III means less than about 6% (w/w) combined total weight for Form II and Form III compared to the combined total weight of Form I, Form II, and Form III; and wherein Form II of 2-{4-[(3S)-piperidin-3-yl]phenyl}-2H-indazole-7-carboxamide tosylate, non-stoichiometric hydrate is characterized by an X-ray powder diffraction (XRPD) pattern comprising diffraction angles at 2θ values of 9.7±0.3, 12.8±0.3, 17.9±0.3, 19.7±0.3, and 21.8±0.3 degrees; and Form III of 2-{4-[(3S)-piperidin-3-yl]phenyl}-2H-indazole-7-carboxamide tosylate anhydrate is characterized by an X-ray powder diffraction (XRPD) pattern comprising diffraction angles at 2θ values of 17.8±0.2, 19.0±0.2, and 22.8±0.2 degrees.

2. The crystalline Form I of claim 1, wherein the crystalline Form I of 2-{4-[(3S)-piperidin-3-yl]phenyl}-2H-indazole-7-carboxamide tosylate monohydrate is characterized by an X-ray powder diffraction (XRPD) pattern substantially in accordance with FIG. 1.

3. The crystalline Form I of claim 1, wherein the crystalline Form I is further characterized by an X-ray powder diffraction (XRPD) pattern comprising diffraction angles at 2θ values of 12.4±0.2, 13.2±0.2, 17.4±0.2, 18.4±0.2, 21.0±0.2, 25.6±0.2, and 26.9±0.2 degrees.

4. The crystalline Form I of claim 1, wherein the crystalline Form I is further characterized by an X-ray powder diffraction (XRPD) pattern comprising at least three diffraction angles selected from a group consisting of 2θ values of 12.4±0.2, 13.2±0.2, 17.4±0.2, 18.4±0.2, 21.0±0.2, 25.6±0.2, and 26.9±0.2 degrees.

5. The crystalline Form I of claim 1, wherein the crystalline Form I is further characterized by an X-ray powder diffraction (XRPD) pattern comprising at least four diffraction angles selected from a group consisting of 2θ values of 12.4±0.2, 13.2±0.2, 17.4±0.2, 18.4±0.2, 21.0±0.2, 25.6±0.2, and 26.9±0.2 degrees.

6. The crystalline Form I of claim 1, wherein the crystalline Form I is characterized by a scanning differential calorimetry pattern substantially as shown in FIG. 2.

7. The crystalline Form I of claim 1, wherein the crystalline Form I is characterized by a Raman spectroscopy pattern substantially as shown in FIG. 3.

8. The crystalline Form I of claim 1, wherein the crystalline Form I is characterized by a dynamic water vapor sorption pattern substantially as shown in FIG. 5.

9. The crystalline Form I of claim 1, wherein the crystalline Form I is characterized by an infrared spectroscopy pattern substantially as shown in FIG. 4.

10. The crystalline Form I of claim 1, wherein the crystalline Form I is prepared by a method comprising dissolving a composition comprising Form II of 2-{4-[(3S)-piperidin-3-yl]phenyl}-2H-indazole-7-carboxamide tosylate, non-stoichiometric hydrate or Form III of 2-{4-[(3S)-piperidin-3-yl]phenyl}-2H-indazole-7-carboxamide tosylate anhydrate, or a mixture thereof, in a solvent having a water:organic solvent ratio of about 10:1 to about 400:1 (v/v), and crystallizing the crystalline Form I.

11. A method of treating a patient diagnosed with ovarian cancer, fallopian tube cancer, epithelial ovarian cancer, recurrent ovarian cancer, prostate cancer, colon cancer, or rectal cancer comprising:
   administering to the patient a pharmaceutically acceptable dose of a crystalline Form I of 2-{4-[(3S)-piperidin-3-yl]phenyl}-2H-indazole-7-carboxamide tosylate monohydrate substantially free of Form II of 2-{4-[(3S)-piperidin-3-yl]phenyl}-2H-indazole-7-carboxamide tosylate, non-stoichiometric hydrate and Form III of 2-{4-[(3S)-piperidin-3-yl]phenyl}-2H-indazole-7-carboxamide tosylate anhydrate;
   wherein the crystalline Form I of 2-{4-[(3S)-piperidin-3-yl]phenyl}-2H-indazole-7-carboxamide tosylate monohydrate is characterized by an X-ray powder diffraction (XRPD) pattern comprising diffraction angles at 2θ values of 9.5±0.2, 24.9±0.2, and 26.0±0.2 degrees; and
   wherein substantially free of Form II and Form III means less than about 6% (w/w) combined total weight for Form II and Form III compared to the combined total weight of Form I, Form II, and Form III; and
   wherein Form II of 2-{4-[(3S)-piperidin-3-yl]phenyl}-2H-indazole-7-carboxamide tosylate, non-stoichiometric hydrate is characterized by an X-ray powder diffraction (XRPD) pattern comprising diffraction angles at 2θ values of 9.7±0.3, 12.8±0.3, 17.9±0.3, 19.7±0.3, and 21.8±0.3 degrees; and
   Form III of 2-{4-[(3S)-piperidin-3-yl]phenyl}-2H-indazole-7-carboxamide tosylate anhydrate is characterized by an X-ray powder diffraction (XRPD) pattern comprising diffraction angles at 2θ values of 17.8±0.2, 19.0±0.2, and 22.8±0.2 degrees.

12. The method of claim 11, wherein the crystalline Form I of 2-{4-[(3S)-piperidin-3-yl]phenyl}-2H-indazole-7-carboxamide tosylate monohydrate is characterized by an X-ray powder diffraction (XRPD) pattern substantially in accordance with FIG. 1.

13. The method of claim 11, wherein the crystalline Form I is further characterized by an X-ray powder diffraction (XRPD) pattern comprising diffraction angles at 2θ values of 12.4±0.2, 13.2±0.2, 17.4±0.2, 18.4±0.2, 21.0±0.2, 25.6±0.2, and 26.9±0.2 degrees.

14. The method of claim 11, wherein the crystalline Form I is further characterized by an X-ray powder diffraction (XRPD) pattern comprising at least three diffraction angles selected from a group consisting of 2θ values of 12.4±0.2, 13.2±0.2, 17.4±0.2, 18.4±0.2, 21.0±0.2, 25.6±0.2, and 26.9±0.2 degrees.

15. The method of claim 11, wherein the crystalline Form I is further characterized by an X-ray powder diffraction (XRPD) pattern comprising at least four diffraction angles selected from a group consisting of 2θ values of 12.4±0.2, 13.2±0.2, 17.4±0.2, 18.4±0.2, 21.0±0.2, 25.6±0.2, and 26.9±0.2 degrees.

16. The method of claim 11, wherein the crystalline Form I is characterized by a scanning differential calorimetry pattern substantially as shown in FIG. 2.

17. The method of claim 11, wherein the crystalline Form I is characterized by a Raman spectroscopy pattern substantially as shown in FIG. 3.

18. The method of claim 11, wherein the crystalline Form I is characterized by a dynamic water vapor sorption pattern substantially as shown in FIG. 5.

19. The method of claim 11, wherein the crystalline Form I is characterized by an infrared spectroscopy pattern substantially as shown in FIG. 4.

20. The method of claim 11, wherein the crystalline Form I is prepared by a method comprising dissolving a composition comprising Form II of 2-{4-[(3S)-piperidin-3-yl]phenyl}-2H-indazole-7-carboxamide tosylate, non-stoichiometric hydrate or Form III of 2-{4-[(3S)-piperidin-3-yl]phenyl}-2H-indazole-7-carboxamide tosylate anhydrate, or a mixture thereof, in a solvent having a water:organic solvent ratio of about 10:1 to about 400:1 (v/v), and crystallizing the crystalline Form I.

* * * * *